United States Patent
Okamoto et al.

(10) Patent No.: US 12,421,317 B2
(45) Date of Patent: Sep. 23, 2025

(54) POLYNUCLEOTIDES ENCODING ANTI-GLUCAGON-LIKE PEPTIDE 1 RECEPTOR (GLP1R) ANTAGONIST ANTIBODIES

(71) Applicant: Regeneron Pharmaceuticals, Inc., Tarrytown, NY (US)

(72) Inventors: Haruka Okamoto, Ardsley, NY (US); Jee H. Kim, Ardsley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/542,929

(22) Filed: Dec. 18, 2023

(65) Prior Publication Data

US 2024/0117060 A1  Apr. 11, 2024

Related U.S. Application Data

(62) Division of application No. 17/317,056, filed on May 11, 2021, now Pat. No. 11,884,736.

(60) Provisional application No. 63/023,307, filed on May 12, 2020.

(51) Int. Cl.
| | |
|---|---|
| *C07K 16/28* | (2006.01) |
| *A61K 9/00* | (2006.01) |
| *A61K 39/00* | (2006.01) |
| *A61P 3/08* | (2006.01) |

(52) U.S. Cl.
CPC ........ *C07K 16/2869* (2013.01); *A61K 9/0019* (2013.01); *A61P 3/08* (2018.01); *A61K 2039/505* (2013.01); *A61K 2039/54* (2013.01); *C07K 2317/21* (2013.01); *C07K 2317/565* (2013.01); *C07K 2317/76* (2013.01); *C07K 2317/92* (2013.01)

(58) Field of Classification Search
CPC ............ C07K 16/2869; C07K 2317/21; C07K 2317/33; C07K 2317/565; C07K 2317/76; C07K 2317/92; C07K 2317/94; A61K 9/0019; A61K 2039/505; A61K 2039/54; A61P 3/08

See application file for complete search history.

(56) References Cited

U.S. PATENT DOCUMENTS

| | | |
|---|---|---|
| 6,596,541 B2 | 7/2003 | Murphy et al. |
| 8,246,995 B2 | 8/2012 | Dai et al. |
| 8,257,740 B1 | 9/2012 | Sung et al. |
| 8,389,689 B2 | 3/2013 | O'Neil et al. |
| 2004/0101920 A1 | 5/2004 | Radziejewski et al. |
| 2007/0280945 A1 | 12/2007 | Stevens et al. |
| 2010/0331527 A1 | 12/2010 | Davis et al. |
| 2011/0195454 A1 | 8/2011 | McWhirter et al. |

FOREIGN PATENT DOCUMENTS

| | | |
|---|---|---|
| WO | 20050103081 A2 | 11/2005 |
| WO | 2018094404 A1 | 5/2018 |
| WO | 2019051501 A1 | 3/2019 |

OTHER PUBLICATIONS

Al-Lazikani et al., "Standard conformations for the canonical structures of immunoglobulins", J. Mol. Biol. (1997), 273(4):927-948.
Altschul et al., "Gapped BLAST and PSI-BLAST: a new generation of protein database search programs," Nucleic Acids Res. (1997), 25(17):3389-3402.
Altschul et al., "Basic Local Alignment Seach Tool," J. Mol. Biol. (1990), 215:403-10.
Arruebo et al., "Antibody-conjugated nanoparticles for biomedical applications," J. Nanomat. (2009), vol. 2009, Article ID 439389, 24 pages.
Bendig, "Humanization of Rodent Monoclonal Antibodies by CDR Grafting," Methods: A Companion to Methods in Enzymology, Academy Press, Inc. (1995), *: 83-93.
Biggs et al., "Development and characterisation of a novel glucagon like peptide-1 receptor anitbody," Diabetologia (2018), 61: 711-21.
Casset et al., "A peptide mimetic of an anti-CD4 monoclonal antibody by rational design," Biochemical and Biophysical Research Communications (2003), 307: 198-205.
Chen et al., "Enhancement and destruction of antibody function by somatic mutation; unequal occurrence is controlled by V gene combinatorial associations," The EMBO Journal (1995), 14(12): 2784-94.
Colman, P.M., "Effects of amino acid sequnce changes on antibody-antigen interactions," Research in Immunology, Elesevier, NY (1994), 145(1): 33-36.
Donnelly, "The structure and function of the glucagon-like peptide-1 receptor and its ligands", Br J Pharmacol (2012), 166(1):27-41.
Ehring, "Hydrogen exchange/electrospray ionization mass spectrometry studies of structural features of proteins and protein/protein interactions", Anal Biochem (1999), 267(2):252-259.
Eisenberg et al., "ASMBS Position Statement on Postprandial Hyperinsulinemic Hypoglycemia after Bariatric Surgery", Surg Obes Relat Dis. (2017), 13(3):371-378.

(Continued)

*Primary Examiner* — Robert S Landsman
(74) *Attorney, Agent, or Firm* — Fox Rothschild LLP; Liang Zeng Yan

(57) ABSTRACT

The present disclosure relates to antibodies or antigen-binding fragments thereof that bind specifically to the glucagon-like peptide 1 receptor (GLP1R) protein, and methods of use thereof. In various embodiments, the antibodies or antigen-binding fragments thereof are fully human antibodies that bind to GLP1R. In some embodiments, the antibodies or antigen-binding fragments thereof are useful for attenuating GLP1R activity, thus providing a means of treating, preventing, or alleviating a disease, disorder or condition associated with GLP1R in humans. In some embodiments, the antibodies or antigen-binding fragments thereof elevate glucose levels when administered to a subject and thereby treat hypoglycemia, such as post-bariatric hypoglycemia (PBH), by attenuating insulin secretion from pancreatic beta cells and decreasing insulin expression.

15 Claims, 2 Drawing Sheets

Specification includes a Sequence Listing.

(56) References Cited

OTHER PUBLICATIONS

Engen et al., "A powerful new approach that goes beyond deciphering protein structures", Anal Chem. (2001), 73(9):256A-265A.
Gonnet et al., "Exhaustive matching of the entire protein sequence database". Science (1992), 256(5062):1443-45.
Gribsholt et al., "Many complications after Roux-en-Y gastric bypass surgery can be prevented and treated", Ugeskr Laeger (2016), 178(44):V06160415.
Hochleitner et al., "Characterization of a discontinuous epitope of the human immunodeficiency virus (HIV) core protein p24 by epitope excision and differential chemical modification followed by mass spectrometric peptide mapping analysis" Prot. Sci. (2000), 9(3):487-496.
International Search Report and Written Opinion mailed Aug. 16, 2021 for PCT/US2021/031694.
Junghans et al., "Anti-Tac-H, a humanized antibody to the interleukin 2 receptor with new features for immunotherapy in malignant and immune disorders", Cancer Res. (1990), 50(5):1495-1502.
Kabat, "Sequences of Proteins of Immunological Interest," National Institutes of Health, Bethesda, Md. (1991).
Kazane et al., "Self-Assembled Antibody Multimers Through Peptide Nucleic Acid Conjugation," (2013) J. Am. Chem. Soc., 135(1):340-6.
Kellogg et al., "Postgastric bypass hyperinsulinemic hypoglycemia syndrome: characterization and response to a modified diet" (2008), Surg Obes Relat Dis., 4(4):492-99.
Kufer et al., "A revival of bispecific antibodies" Trends Biotechnol. (2004), 22(5):238-244.
Langer, "New methods of drug delivery", Science, (1990) 249(4976):1527-1533.
Lee et al., "Prevalence of and risk factors for hypoglycemic symptoms after gastric bypass and sleeve gastrectomy", Obesity (Silver Spring) (2015), 23(5):1079-84.
Maccallum et al., "Antibody-antigen Interactions: Contact Analysis and Binding Slte Topography," J. Mol. Biol. (1996), 262(5): 732-45.
Marsk et al., "Nationwide cohort study of post-gastric bypass hypoglycaemia including 5,040 patients undergoing surgery for obesity in 1986-2006 in Sweden" Diabetologia (2010), 53(11):2307-11.
Martin et al., "Modeling antibody hypervariable loops: a combined algorithm", Proc. Natl. Acad. Sci. USA (1989), 86(23):9268-9272.
Nambron et al., "Post Bariatric Surgery hypoglycemia—a descriptive analysis", WMJ (2013), 112(3):136.
Padlan et al., "Identification of specificity-determining residues in antibodies" FASEB J. (1995), 9(1):133-139.
Paul, W.E. "Fundamental Immunology," 3rd ed. Raven Press, NY (1993), 9: 292-95.
Pearson, "Using the FASTA program to search protein and DNA sequence databases.", Methods Mol. Biol. (1994), 24: 307-331.
Powell et al., "Compendium of excipients for parenteral formulations" PDA, J Pharm Sci Technol, (1998) 52(5):238-311.
Reddy et al., "Elimination of Fc receptor-dependent effector functions of a modified lgG4 monoclonal antibody to human CD4", J. Immunol. (2000), 164(4):1925-1933.
Reineke, "Antibody Epitope Mapping Using Arrays of Synthetic Peptides. In: Lo B.K.C. (eds) Antibody Engineering" Methods Mol. Biol. (2004), 248:443-63, Humana Press. https://doi.org/10.1385/1-59259-666-5:443.
Rudikoff et al., "Single amino acid substitution altering antigen-binding specificity," Proc. Natl. Acad. Sci. USA (1982), 79: 1979-83.
Shields et al., "Lack of fucose on human lgG1 N-linked oligosaccharide improves binding to human Fcgamma RIII and antibody-dependent cellular toxicity" J Biol Chem. (2002), 277(30):26733-40.
Sun et al., "Prevalence and risk factors for symptoms suggestive of hypoglycemia and early dumping syndrome after sleeve gastrectomy". Surg Obes Relat Dis. (2019), 15(9):1439-1446.
Tutt et al., "Trispecific F(ab')3 derivatives that use cooperative signaling via the TCR/CD3 complex and CD2 to activate and redirect resting cytotoxic T cells", J. Immunol. (1991), 147(1):60-69.
Vajdos et al., "Comprehensive functional maps of the antigen-binding site of an anti-ErbB2 antibody obtained with shotgun scanning mutagenesis", J Mol Biol (2002), 320(2):415-428.
Webpage at www.biovision.com (accessed Jul. 4, 2023) (3 pages).
Webpage at www.nuvusbio.com (accessed Jul. 4, 2023) (2 pages).
Webpage at www.ThermoFisher.com (accessed Jul. 4, 2023) (5 pages).
Wu et al., "Receptor-mediated in vitro gene transformation by a soluble DNA carrier system", J Biol Chem, (1987) 262(10):4429-4432.
U.S. Appl. No. 17/317,056, filed May 11, 2021.
U.S. Appl. No. 63/023,307, filed May 12, 2020.

POLYNUCLEOTIDES ENCODING ANTI-GLUCAGON-LIKE PEPTIDE 1 RECEPTOR (GLP1R) ANTAGONIST ANTIBODIES

CROSS-REFERENCE TO RELATED APPLICATION

This application is a divisional of U.S. patent application Ser. No. 17/317,056 filed May 11, 2021 (now U.S. Pat. No. 11,884,736), which claims the benefit of priority to U.S. Provisional Patent Application No. 63/023,307 filed May 12, 2020, the disclosures of which is are hereby incorporated by reference in their entirety.

SEQUENCE LISTING

The sequence listing of the present application is submitted electronically as a computer readable sequence listing in XML format with a file name of "SeqList10790.xml," a creation date of Nov. 22, 2023, and a size of 86,251 bytes. This sequence listing submitted is part of the specification and is hereby incorporated by reference in its entirety. The following sequences have a length that is below the minimum length permitted under ST.26 format: gatgcatcc (SEQ ID NO: 13), DAS (SEQ ID NO: 14), ggtgcatcc (SEQ ID NO: 51), GAS (SEQ ID NO: 52).

FIELD

The present disclosure relates to antagonist antibodies and antigen-binding fragments thereof that specifically bind to glucagon-like peptide 1 receptor (GLP1R), and therapeutic methods of use thereof, including treatment of hypoglycemia.

BACKGROUND

Bariatric surgeries represent effective treatment options for patients with severe obesity. Each year, approximately 44,000 gastric bypass surgeries and 138,000 gastrectomies are performed in the United States alone. Successful weight loss after bariatric surgeries often leads to improved insulin sensitivity. Improved insulin sensitivity coupled with an elevated level of glucagon-like peptide 1 (GLP1) precipitates postprandial, hyperinsulinemic hypoglycemia in a subset of surgery recepients. Hypoglycemia is generally characterized by low plasma glucose levels at the time of symptoms, and the relief of symptoms upon raising of glucose levels. Post-bariatric hypoglycemia (PBH) is characterized by postprandial hypoglycemia that develops 1-3 hours after a meal. GLP1 is secreted in response to food consumption and activates GLP1 receptor (GLP1R) on pancreatic beta-cells to induce insulin secretion. Thus, increased GLP1 plays a critical role in the development of PBH. As the number of bariatric surgical procedures continues to increase worldwide, a severe complication—hyperinsulinemic hypoglycemia—is increasingly reported. For instance, symptomatic hypoglycemia is reported to occur in 0.2~15% of gastric bypass and 1~7% of gastrectomy recipients 0.5~10 years post-surgery. Kellogg et al., *Surg Obes Relat Dis.*, 4(4):492-99 (2008); Marsk et al., *Diabetologia*, 53(11):2307-11 (2010); Nambron et al., *WMJ*, 112(3):136 (2013); Lee et al., *Obesity (Silver Spring)*, 23(5):1079-84 (2015); Gribsholt et al., *Ugeskr Laeger*, 178(44) (2016); Sun et al., *Surg Obes Relat Dis.*, 15(9):1439-1446 (2019).

GLP1 plays a critical role in PBH because the surgeries lead to an increase in GLP1 secretion due to faster passage of foods into the small intestine, where GLP1-producing L-cells are located. While increased GLP1 generally helps post-operative weight loss in obese patients, symptoms of hypoglycemia can also occur, including adrenergic effects (e.g., tremor, palpitations, anxiety), cholinergic effects (e.g., sweating, hunger, paresthesia), and neuroglycopenia effects (e.g., impaired cognition, seizures, and loss of consciousness), especially among individuals who achieve significant weight loss post surgery. Patients with recurrent hypoglycemia may experience abrupt onset of neuroglycopenia, which can result in serious falls, motor vehicle accidents, seizures, and loss of consciousness. Severe PBH is debilitating and significantly impairs quality of life. Current treatment options for PBH include dietary modifications, acarbose (starch digestion blocker), somatostatin analogue, nifedipine (Ca channel blocker), diazoxide, and placement of gastrostomy tube. Eisenberg et al., *Surg Obes Relat Dis.*, 13(3):371-378 (2017). Increasing rates of morbid obesity indicate that PBH cases will be growing as a complication of bariatric surgery.

Other disorders, diseases, and conditions can also lead to low plasma glucose levels. For example, dumping syndrome is a frequent complication of upper abdominal (e.g., bariatric, esophageal, or gastric) surgery, where GLP1 appears to play a major role. Dumping syndrome is estimated to occur in up to 40% of bariatric surgery patients (Roux-en-Y gastric bypass or sleeve gastrectomy), up to 50% of patients receiving esophagectomy to treat esophageal cancer, and up to 75% of patients receiving gastrectomy to treat stomach cancer and peptic ulcers. A diagnosis of dumping syndrome can occur months to years after surgery. A GLP1-driven hyperinsulinemic response after carbohydrate ingestion leads to hypoglycemia-related symptoms, such as neuroglycopenia (fatigue, weakness, confusion, hunger and syncope) and autonomic/adrenergic reactivity (perspiration, palpitations, tremor, and irritability).

Hypoglycemia, including PBH, can occur with a range of severity. Quality of life is substantially impacted by severe hypoglycemia such that affected patients cannot be left alone, transport or care for themselves or others. There is no approved or effective pharmacologic therapy for PBH or severe hypoglycemia that is long-acting and that does not lead to hyperglycemia, and surgical intervention has not been universally successful in reversing hypoglycemia. Consequently, there remains a significant and unmet need for a therapeutic that effectively elevates blood glucose levels and thus can serve as a useful treatment for hypoglycemia of any origin, including PBH.

SUMMARY

The present disclosure provides antibodies and antigen-binding fragments thereof that specifically bind the glucagon-like peptide 1 receptor (GLP1R) protein. In certain embodiments, the GLP1R antibodies are fully human antibodies that bind to GLP1R with high affinity and block GLP1R binding and/or activity or destabilize the activated conformation. The antibodies or antigen-binding fragments thereof of the present disclosure are useful, inter alia, for inactivating or decreasing the activity of GLP1R protein. In certain embodiments, the antibodies or antigen-binding fragments thereof are useful in preventing, treating or ameliorating at least one symptom or indication of a GLP1R-associated disease or disorder in a subject. In certain embodiments, the antibodies or antigen-binding fragments thereof may be administered prophylactically or therapeutically to a subject having or at risk of having a GLP1R-associated disease or disorder, such as PBH or other types of hypoglycemia of any origin. In specific embodiments, the antibodies or antigen-binding fragments thereof are used to elevate glucose levels in a subject in need thereof. Such antibodies or antigen-binding fragments thereof can be used as therapy for a disorder such as hypoglycemia of any origin (e.g., post-bariatric hypoglycemia or hypoglycemia resulting from other upper abdominal surgeries such as esophagectomy, gastrectomy for stomach cancer and peptic ulcers, and the like, or hypoglycemia resulting from inherent etiologies such as genetic abnormalities) when administered to a subject in need thereof. In some embodiments, the GLP1 antagonist antibodies or antigen-binding fragments of the present disclosure have a longer half-life and reduced immunogenicity as compared to other therapies, such as Exendin (9-39) (Avexitide, Eiger BioPharmaceuticals). In some embodiments, the antibodies or antigen-binding fragments disclosed herein bind to GLP1R with high affinity and have improved pharmacokinetic properties as compared to standard-of-care drugs.

The antibodies and antigen-binding fragments disclosed herein bind specifically to GLP1R in an antagonist manner, i.e., in a manner that attenuates or prevents or blocks GLP1R binding and/or activity. The antibodies are efficacious in elevating blood glucose levels and maintaining normalized levels when administered to a subject in need thereof. A single dose of an antibody of the present disclosure led to sustained normalized blood glucose levels for 46 days in mice. Such antibodies can be used to provide superior efficacy, along with less frequent dosing, in a subject with a GLP1R-associated disease or disorder (e.g., hypoglycemia).

The antibodies of the present disclosure can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, *J. Immunol.* 164:1925-1933). In certain embodiments, the antibodies may be bi-specific.

In one aspect, the present disclosure provides isolated recombinant monoclonal antibodies or antigen-binding fragments thereof that bind specifically to GLP1R.

In some embodiments, the antibodies are fully human monoclonal antibodies.

The GLP1R antagonists of the present disclosure are useful, inter alia, for decreasing activation of GLP1R. In some embodiments, the GLP1R antagonists function by decreasing insulin secretion and lowering blood glucose levels. In some embodiments, the GLP1R antagonists function by attenuating glucose-induced secretion of insulin from pancreatic beta cells and decreasing insulin expression. In certain embodiments, the GLP1R antagonists are useful in preventing, treating or ameliorating at least one symptom of a hypoglycemia-associated disease or disorder (e.g., PBH) in a subject.

In some embodiments, the disclosed anti-GLP1R antagonist antibodies and antigen-binding fragments thereof substantially or completely correct exendin-4 induced hypoglycemia for over 45 days after single dosing, as illustrated in Example 5.

Exemplary GLP1R antagonist antibodies of the present disclosure are listed in Tables 1 and 2 herein. Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary antibodies. Table 2 sets forth the nucleic acid sequence identifiers of the HCVRs, LCVRs, HCDR1, HCDR2 HCDR3, LCDR1, LCDR2 and LCDR3 of the exemplary antibodies.

The present disclosure provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present disclosure also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present disclosure also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR amino acid sequence pair contained within any of the exemplary anti-GLP1R antibodies listed in Table 1. In certain embodiments, the HCVR/LCVR amino acid sequence pair is selected from one of SEQ ID NOs: 2/10 (e.g., mAb36986), 22/30 (e.g., mAb37639), and 40/48 (e.g., mAb37645).

The present disclosure also provides antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present disclosure provides antibodies or antigen-binding fragments thereof comprising a HCVR and a LCVR, said HCVR comprising an amino acid sequence listed in Table 1, said amino acid sequence having one, two, three, four, five, six, seven, eight, nine, ten, eleven or twelve amino acid substitutions. In another example, the present disclosure provides antibodies or antigen-binding fragments thereof comprising a HCVR and a LCVR, said LCVR comprising an amino acid sequence listed in Table 1, said amino acid sequence having one, two, three, four, five, six, seven, eight, nine or ten amino acid substitutions. In one embodiment, the present disclosure provides anti-GLP1R antibodies or antigen-binding fragments thereof comprising a HCVR and a LCVR, said HCVR comprising an amino acid sequence listed in Table 1, said amino acid sequence having at least one amino acid substitution, and/or said LCVR comprising an amino acid sequence listed in Table 1, said amino acid sequence having at least one amino acid substitution.

The present disclosure also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising an HCDR1 and an LCDR1 amino acid sequence pair (HCDR1/LCDR1) comprising any of the HCDR1 amino acid sequences listed in Table 1 paired with any of the LCDR1 amino acid sequences listed in Table 1. According to certain embodiments, the present disclosure provides antibodies, or antigen-binding fragments thereof, comprising an HCDR1/LCDR1 amino acid sequence pair contained within any of the exemplary anti-GLP1R antibodies listed in Table 1. In certain embodiments, the HCDR1/LCDR1 amino acid sequence pair is selected from the group consisting of SEQ ID NOs: 4/12 (e.g., mAb36986), 24/32 (e.g., mAb37639), and 42/50 (e.g., mAb37645).

The present disclosure also provides antibodies, or antigen-binding fragments thereof, comprising an HCDR2 and an LCDR2 amino acid sequence pair (HCDR2/LCDR2) comprising any of the HCDR2 amino acid sequences listed in Table 1 paired with any of the LCDR2 amino acid sequences listed in Table 1. According to certain embodiments, the present disclosure provides antibodies, or antigen-binding fragments thereof, comprising an HCDR2/LCDR2 amino acid sequence pair contained within any of the exemplary anti-GLP1R antibodies listed in Table 1. In certain embodiments, the HCDR2/LCDR2 amino acid sequence pair is selected from the group consisting of SEQ ID NOs: 6/14 (e.g., mAb36986), 26/14 (e.g., mAb37639), and 44/52 (e.g., mAb37645).

The present disclosure also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-GLP1R antibodies listed in Table 1. In certain embodiments, the HCDR3/LCDR3 amino acid sequence pair is selected from the group consisting of SEQ ID NOs: 8/16 (e.g., mAb36986), 28/34 (e.g., mAb37639), and 46/54 (e.g., mAb37645).

The present disclosure also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid.

In certain embodiments, the present disclosure provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid.

The present disclosure also provides antibodies, or antigen-binding fragments thereof, comprising a heavy chain (HC) comprising an amino acid sequence selected from any of the HC amino acid sequences listed in Table 3, or a substantially similar sequence thereof having at least 90%, at least 95%, at least 98% or at least 99% sequence identity thereto.

The present disclosure also provides antibodies, or antigen-binding fragments thereof, comprising a light chain (LC) comprising an amino acid sequence selected from any of the LC amino acid sequences listed in Table 3, or a substantially similar sequence thereof having at least 90%, at least 95%, at least 98% or at least 99% sequence identity thereto.

The present disclosure also provides antibodies, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present invention provides antibodies, or antigen-binding fragments thereof, comprising an HC/LC amino acid sequence pair contained within any of the exemplary anti-GLP1R antibodies listed in Table 3. In certain embodiments, the HC/LC amino acid sequence pair is selected from the group consisting of SEQ ID NOs: 18/20, 36/38 and 56/58.

The present disclosure also provides antibodies, or antigen-binding fragments thereof, comprising a set of six CDRs (i.e., HCDR1/HCDR2/HCDR3/LCDR1/LCDR2/LCDR3) contained within any of the exemplary antibodies listed in Table 1. In certain embodiments, the HCDR1/HCDR2/HCDR3/LCDR1/LCDR2/LCDR3 amino acid sequence set is selected from the group consisting of SEQ ID NOs: 4/6/8/12/14/16 (e.g., mAb36986), 24/26/28/32/14/34 (e.g., mAb37639), and 42/44/46/50/52/54 (e.g., mAb37645). In a related embodiment, the present disclosure provides antibodies, or antigen-binding fragments thereof, comprising a set of six CDRs (i.e., HCDR1/HCDR2/HCDR3/LCDR1/LCDR2/LCDR3) contained within an HCVR/LCVR amino acid sequence pair as defined by any of the exemplary antibodies listed in Table 1. For example, the present disclosure includes antibodies, or antigen/binding fragments thereof, comprising the HCDR1/HCDR2/

HCDR3/LCDR1/LCDR2/LCDR3 amino acid sequences set contained within an HCVR/LCVR amino acid sequence pair selected from the group consisting of SEQ ID NOs: 2/10 (e.g., mAb36986), 22/30 (e.g., mAb37639), and 40/48 (e.g., mAb37645).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the present disclosure includes an antibody or antigen-binding fragment thereof that binds specifically to GLP1R, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) an amino acid sequence selected from the group consisting of SEQ ID NOs: 2, 22, and 40; (ii) an amino acid sequence having at least 90% identity to the amino acid sequence selected from the group consisting of SEQ ID NOs: 2, 22, and 40; (iii) an amino acid sequence having at least 95% identity to the amino acid sequence selected from the group consisting of SEQ ID NOs: 2, 22, and 40; or (iv) an amino acid sequence selected from the group consisting of SEQ ID NOs: 2, 22, and 40, said amino acid sequence having no more than 12 amino acid substitutions; and the LCVR comprises: (i) an amino acid sequence selected from the group consisting of SEQ ID NOs: 10, 30, and 48; (ii) an amino acid sequence having at least 90% identity to the amino acid sequence selected from the group consisting of SEQ ID NOs: 10, 30, and 48; (iii) an amino acid sequence having at least 95% identity to the amino acid sequence selected from the group consisting of SEQ ID NOs: 10, 30, and 48; or (iv) an amino acid sequence selected from the group consisting of SEQ ID NOs: 10, 30, and 48, said amino acid sequence having no more than 12 amino acid substitutions.

The present disclosure includes anti-GLP1R antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In certain embodiments, the present disclosure provides antibodies and antigen-binding fragments thereof that exhibit pH-dependent binding to GLP1R. For example, the present disclosure includes antibodies and antigen-binding fragment thereof that bind GLP1R with higher affinity at neutral pH than at acidic pH (i.e., reduced binding at acidic pH).

The present disclosure also provides for antibodies and antigen-binding fragments thereof that compete for specific binding to GLP1R with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present disclosure also provides antibodies and antigen-binding fragments thereof that cross-compete for binding to GLP1R with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present disclosure also provides antibodies and antigen-binding fragments thereof that bind to the same epitope as a reference antibody or antigen-binding fragment thereof comprising three CDRs of a HCVR and three CDRs of a LCVR, wherein the HCVR and LCVR each has an amino acid sequence selected from the HCVR and LCVR sequences listed in Table 1.

The present disclosure also provides antibodies and antigen-binding fragments thereof that decrease or destabilize GLP1R binding to GLP1. In some embodiments, the antibody or antigen-binding fragment thereof that blocks GLP1R binding to GLP1 may bind to the same epitope on GLP1R as GLP1 or may bind to a different epitope on GLP1R as GLP1.

In certain embodiments, the antibodies or antigen-binding fragments of the present disclosure are bi-specific comprising a first binding specificity to a first epitope of GLP1R and a second binding specificity to a second epitope of GLP1R wherein the first and second epitopes are distinct and non-overlapping.

In certain embodiments, the present disclosure provides an isolated antibody or antigen-binding fragment thereof that has one or more of the following characteristics: (a) is a fully human monoclonal antibody; (b) binds to human GLP1R at 25° C. with a dissociation constant (K D) of less than 6 nM, as measured in a surface plasmon resonance (SPR) assay; (c) binds to human GLP1R at 37° C. with a $K_D$ of less than 20 nM, as measured in a SPR assay; (d) binds to monomeric cynomolgus GLP1R at 25° C. with a $K_D$ of less than 20 nM, as measured in a SPR assay; (e) binds to monomeric cynomolgus GLP1R at 37° C. with a $K_D$ of less than 60 nM, as measured in a SPR assay; (f) binds to hdesA-GLP1_GLP1R-MMH at 25° C. with a $K_D$ of less than 18 nM, as measured in a SPR assay; (g) binds to hdesA-GLP1_GLP1R-MMH at 37° C. with a $K_D$ of less than 75 nM, as measured in a SPR assay; (h) binds to monomeric mouse GLP1R at 25° C. with a $K_D$ of less than 22 nM, as measured in a SPR assay; (i) binds to monomeric mouse GLP1R at 37° C. with a $K_D$ of less than 75 nM, as measured in a SPR assay; (j) blocks the interaction of GLP1 and GLP1R with an $IC_{50}$ value of less than about 10 nM as measured in an in vitro receptor/ligand binding assay at 37° C.; (k) reduces GLP1-induced hypoglycemia without causing hyperglycemia; and (l) elevates blood glucose to a normalized level.

In another aspect, the present disclosure provides nucleic acid molecules encoding anti-GLP1R antibodies or fragments thereof. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto. The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs HCDR1-HCDR2-HCDR3), wherein the HCDR1-HCDR2-HCDR3 amino acid sequence set is as defined by any of the exemplary antibodies listed in Table 1.

The present disclosure also provides nucleic acid molecules encoding an LCVR, wherein the LCVR comprises a set of three CDRs LCDR1-LCDR2-LCDR3), wherein the LCDR1-LCDR2-LCDR3 amino acid sequence set is as defined by any of the exemplary antibodies listed in Table 1.

The present disclosure also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect, the nucleic acid molecule encodes an HCVR and LCVR, wherein the HCVR and LCVR are both derived from the same anti-GLP1R antibody listed in Table 1.

The present disclosure provides nucleic acid molecules encoding any of the heavy chain amino acid sequences listed in Table 3. The present invention also provides nucleic acid molecules encoding any of the light chain amino acid sequences listed in Table 3. The present invention also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present disclosure provides recombinant expression vectors capable of expressing a polypeptide comprising a heavy and/or light chain variable region of an antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 2. In certain embodiments, the present disclosure provides expression vectors comprising: (a) a nucleic acid molecule comprising a nucleic acid sequence encoding a HCVR of an antibody that binds GLP1R, wherein the HCVR comprises an amino acid sequence selected from the group consisting of sequences listed in Table 1; and/or (b) a nucleic acid molecule comprising a nucleic acid sequence encoding a LCVR of an antibody that binds GLP1R, wherein the LCVR comprises an amino acid sequence selected from the group consisting of sequences listed in Table 1. Also included within the scope of the present disclosure are host cells into which such vectors have been introduced, as well as methods of producing the antibodies or portions thereof by culturing the host cells under conditions permitting production of the antibodies or antibody fragments and recovering the antibodies and antibody fragments so produced. In certain embodiments, the host cells comprise a mammalian cell or a prokaryotic cell. In certain embodiments, the host cell is a Chinese Hamster Ovary (CHO) cell or an *Escherichia coli* (*E. coli*) cell. In certain embodiments, the present disclosure provides methods of producing an antibody or antigen-binding fragment thereof. The methods comprise introducing into a host cell an expression vector comprising a nucleic acid sequence encoding a HCVR and/or LCVR of an antibody or antigen-binding fragment thereof of the disclosure operably linked to a promoter; culturing the host cell under conditions favorable for expression of the nucleic acid sequence; and isolating the antibody or antigen-binding fragment thereof from the culture medium and/or host cell.

In certain embodiments, the method comprises introducing into a host cell (e.g., CHO cells) (a) a first expression vector comprising a nucleic acid sequence encoding a HCVR of an antibody or antigen-binding fragment thereof of the disclosure operably linked to a promoter, and (2) a second expression vector comprising a nucleic acid sequence encoding a LCVR of an antibody or antigen-binding fragment thereof of the disclosure operably linked to a promoter; culturing the host cell under conditions favorable for expression of the nucleic acid sequence; and isolating the antibody or antigen-binding fragment thereof from the culture medium and/or host cell. The isolated antibody or antigen-binding fragment thereof may be purified using any of the methods known in prior art.

In another aspect, the present disclosure provides a pharmaceutical composition comprising a therapeutically effective amount of at least one recombinant monoclonal antibody or antigen-binding fragment thereof which specifically binds GLP1R and a pharmaceutically acceptable carrier. In a related aspect, the disclosure features a composition which is a combination of an anti-GLP1R antibody and a second therapeutic agent. In one embodiment, the second therapeutic agent is any agent that is advantageously combined with an anti-GLP1R antibody—e.g., an insulin or insulin receptor inhibitor, a starch digestion blocker (e.g., acarbose), a somatostatin analogue (e.g., octreotide, lanreotide), a calcium channel blocker (e.g., nifedipine), diazoxide, glucagon, a somatostatin receptor type 5 agonist, or a combination thereof. Exemplary agents that may be advantageously combined with an anti-GLP1R antibody include, without limitation, other agents that bind and/or deactivate GLP1R activity (including other antibodies or antigen-binding fragments thereof, etc.) and/or agents which do not directly bind GLP1R but nonetheless treat or ameliorate at least one symptom or indication of a GLP1R-associated disease or disorder (disclosed elsewhere herein). Additional combination therapies and co-formulations involving the anti-GLP1R antagonist antibodies of the present disclosure are disclosed elsewhere herein.

Also provided herein are therapeutic methods for treating a disease or disorder associated with GLP1R in a subject using an anti-GLP1R antagonist antibody or antigen-binding fragment thereof, wherein the therapeutic methods comprise administering a therapeutically effective amount of a pharmaceutical composition comprising an antibody or antigen-binding fragment of an antibody disclosed herein to the subject in need thereof. The disorder treated is any disease or condition which is improved, ameliorated, inhibited or prevented by attenuation of GLP1R activity (e.g., hypoglycemia). In certain embodiments, the disclosure provides methods to prevent or treat a GLP1R-associated disease or disorder comprising administering a therapeutically effective amount of an anti-GLP1R antibody or antigen-binding fragment thereof disclosed herein to a subject in need thereof. In some embodiments, the antibody or antigen-binding fragment thereof may be administered prophylactically or therapeutically to a subject having or at risk of having a GLP1R-associated disease or disorder. In certain embodiments, the antibody or antigen-binding fragment thereof is administered to the subject after upper abdominal surgery. In certain embodiments, the antibody or antigen-binding fragment thereof is administered in combination with a second therapeutic agent to the subject in need thereof. In certain embodiments, the second therapeutic agent may be an agent that helps to counteract or reduce any possible side effect(s) associated with an antibody or antigen-binding fragment thereof disclosed herein, if such side effect(s) should occur. The antibody or fragment thereof may be administered subcutaneously, intravenously, intradermally, intraperitoneally, orally, or intramuscularly. The antibody or fragment thereof may be administered at a dose of about 0.1 mg/kg of body weight to about 100 mg/kg of body weight of the subject. In certain embodiments, an antibody or fragment thereof of the present disclosure may be administered at one or more doses comprising between 10 mg to 600 mg.

The present disclosure also includes use of an anti-GLP1R antibody or antigen-binding fragment thereof of the disclosure in the manufacture of a medicament for the treatment of a disease or disorder that would benefit from the blocking of GLP1R binding and/or activity—hypoglycemia, such as PBH.

Other embodiments will become apparent from a review of the ensuing detailed description.

DETAILED DESCRIPTION

Figure 1:
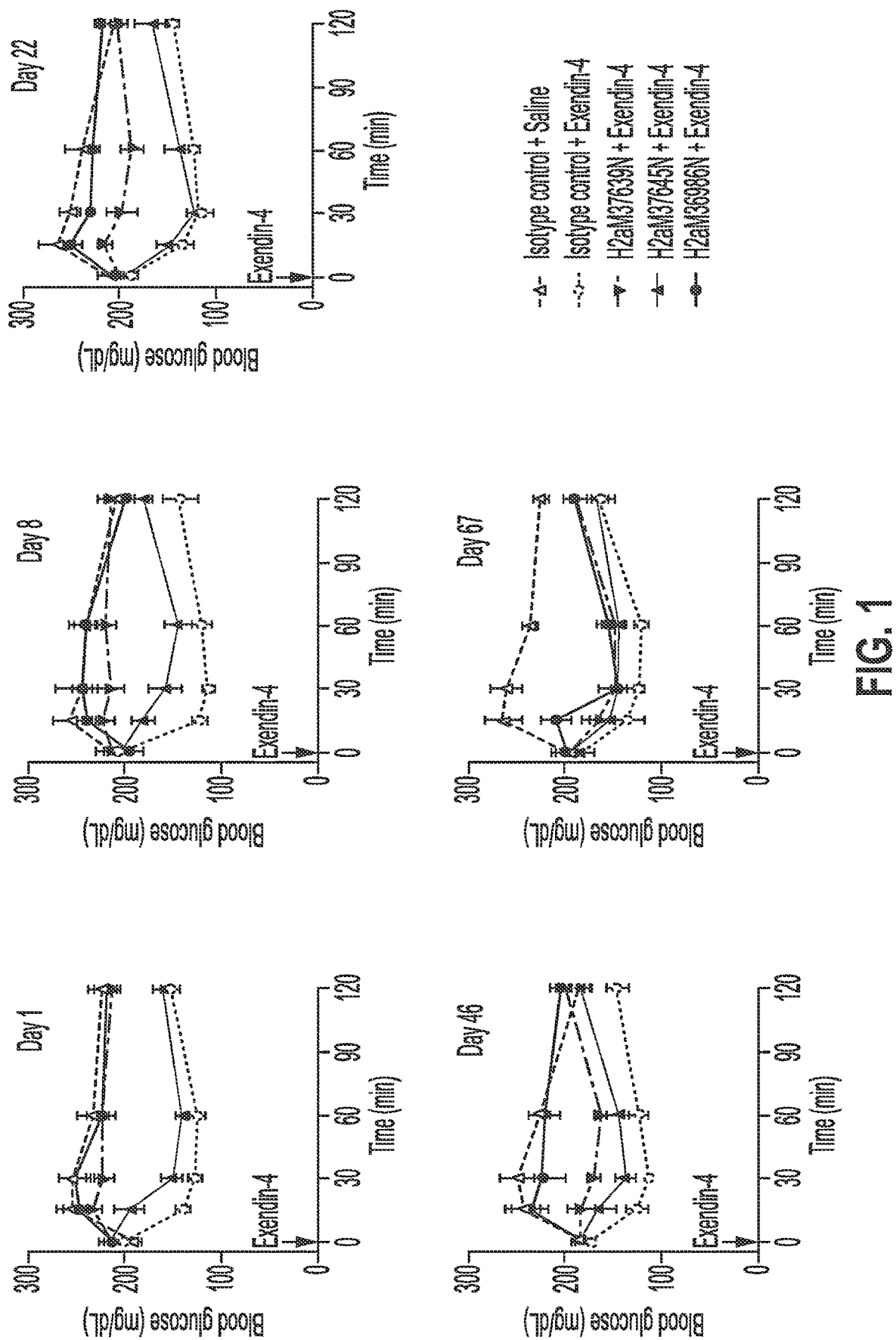
FIG. 1 is a graph showing blood glucose levels (mg/dL) during Exendin-4 challenges performed on 1, 8, 22, 46, and 67 days post antibody administration, as described in the in vivo study set forth in Example 5 herein.

It is to be understood that the present disclosure is not limited to the particular methods and experimental conditions described, as such methods and conditions may vary. It is also to be understood that the terminology used herein is for the purpose of describing particular embodiments only, and is not intended to be limiting, and that the scope of the present disclosure will be limited only by the appended claims. Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, preferred methods and materials are now described. All publications mentioned herein are hereby incorporated by reference in their entirety.

Definitions

The term "GLP1R" refers to the glucagon-like peptide 1 receptor and includes recombinant GLP1R protein or a fragment thereof. GLP1R has a sequence of 463 residues. Donnelly, *Br J Pharmacol,* 166(1):27-41 (2011). Glucagon-like peptide 1 (GLP1) is a 31-amino acid peptide hormone released from intestinal L cells following nutrient consumption. The binding of GLP1 to GLP1R potentiates glucose-induced secretion of insulin from pancreatic beta cells, increases insulin expression, inhibits beta-cell apoptosis, promotes beta-cell neogenesis, reduces glucagon secretion, delays gastric emptying, promotes satiety and increases peripheral glucose disposal.

The term "antibody," as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting the antigen can be identified based on previous studies from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-GLP1R monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic biological properties, reduced immunogenicity, etc. Antibodies and antigen-binding fragments obtained in this general manner are encompassed within the present disclosure.

The present disclosure also includes fully human anti-GLP1R monoclonal antibodies comprising variants of any of the HCVR, LCVR, and/or CDR amino acid sequences disclosed herein having one or more conservative substitutions. For example, the present disclosure includes anti-GLP1R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody," or "fully human antibody," as used herein, is intended to include antibodies having variable and constant regions derived from human germline immunoglobulin sequences. The human mAbs disclosed herein may include amino acid residues not encoded by human germline immunoglobulin sequences (e.g., mutations introduced by random or site-specific mutagenesis in vitro or by somatic mutation in vivo), for example, in the CDRs and in particular CDR3. However, the term "human antibody," or "fully human antibody," as used herein, is not intended to include mAbs in which CDR sequences derived from the germline of another mammalian species (e.g., mouse), have been grafted onto human FR sequences. The term includes antibodies that are recombinantly produced in a non-human mammal, or in cells of a non-human mammal. The term is not intended to include antibodies isolated from or generated in a human subject.

The term "recombinant," as used herein, refers to antibodies or antigen-binding fragments thereof created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to," or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to GLP1R. Moreover, multi-specific antibodies that bind to one domain in GLP1R and one or more additional antigens or a bi-specific that binds to two different regions of GLP1R are nonetheless considered antibodies that "specifically bind," as used herein.

The term "high affinity" antibody refers to those mAbs having a binding affinity to GLP1R, expressed as $K_D$, of at least $10^{-8}$ M; preferably $10^{-9}$ NA; more preferably $10^{-10}$ M, even more preferably $10^{-11}$ M, as measured by surface plasmon resonance, e.g., BIACORE™ or solution-affinity ELISA.

By the term "slow off rate," "Koff" or "kd" is meant an antibody that dissociates from GLP1R, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment," as used herein, refers to one or more fragments of an antibody that retain the ability to bind to GLP1R protein.

In specific embodiments, antibody or antibody fragments of the disclosure may be conjugated to a moiety such a ligand or a therapeutic moiety ("immunoconjugate"), a second anti-GLP1R antibody, or any other therapeutic moiety useful for treating a GLP1R-associated disease or disorder.

An "isolated antibody," as used herein, is intended to refer to an antibody that is substantially free of other antibodies (Abs) having different antigenic specificities (e.g., an isolated antibody that specifically binds GLP1R, or a fragment thereof, is substantially free of Abs that specifically bind antigens other than GLP1R.

A "blocking antibody" or an "antagonist antibody," as used herein (or an "antibody that decreases or attenuates GLP1R activity" or "an antibody that destabilizes the activated conformation"), is intended to refer to an antibody whose binding to GLP1R results in inhibition of at least one biological activity of GLP1R. For example, an antibody of the disclosure may elevate glucose levels upon administration to a subject in need thereof.

The term "surface plasmon resonance," as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$," as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes," as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between two antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., (1992) *Science* 256:1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the present disclosure to a database containing a large number of sequences from different organisms is the computer program BLAST, especially BLASTP or TBLASTN, using default parameters. See, e.g., Altschul et al. (1990) *J. Mol. Biol.* 215:403-410 and (1997) Nucleic Acids Res. 25:3389-3402.

By the phrase "therapeutically effective amount" is meant an amount that produces the desired effect for which it is administered. The exact amount will depend on the purpose of the treatment, and will be ascertainable by one skilled in the art using known techniques (see, e.g., Lloyd (1999) The Art, Science and Technology of Pharmaceutical Compounding).

As used herein, the term "subject" refers to an animal, preferably a mammal, more preferably a human, in need of amelioration, prevention and/or treatment of a GLP1R-associated disease or disorder such as hypoglycemia. The term includes human subjects who have or are at risk of having such a disease or disorder.

As used herein, the terms "treat," "treating," or "treatment" refer to the reduction or amelioration of the severity of at least one symptom or indication of a GLP1R-associated disease or disorder (e.g., hypoglycemia) due to the administration of a therapeutic agent such as an antibody or antigen-binding fragment of the present disclosure to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present disclosure. The therapeutic agent may be administered at a therapeutic dose to the subject.

The terms "prevent," "preventing" or "prevention" refer to inhibition of manifestation of a GLP1R-associated disease or disorder (e.g., hypoglycemia) or any symptoms or indications of such a disease or disorder (e.g., low glucose levels) upon administration of an antibody of the present disclosure.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment," as used herein, refers to one or more fragments of an antibody that retain the ability to specifically bind to GLP1R protein. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; (vii) $V_H$-$C_L$; (viii) $V_L$-$C_H1$; (Ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Preparation of Human Antibodies

Methods for generating human antibodies in transgenic mice are known in the art. Any such known methods can be used in the context of the present disclosure to make human antibodies that specifically bind to GLP1R.

An immunogen comprising any one of the following can be used to generate antibodies to GLP1R protein. In certain embodiments, the antibodies disclosed herein are obtained from mice immunized with a full length, native GLP1R protein or with DNA encoding the protein or fragment thereof. Alternatively, the protein or a fragment thereof may be produced using standard biochemical techniques and modified and used as immunogen. In some embodiments, the immunogen may be a recombinant GLP1R protein or fragment thereof expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to GLP1R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies, or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

Bioequivalents

The anti-GLP1R antagonist antibodies and antibody fragments of the present disclosure encompass proteins having amino acid sequences that vary from those of the described antibodies, but that retain the ability to bind GLP1R protein. Such variant antibodies and antibody fragments comprise one or more additions, deletions, or substitutions of amino acids when compared to parent sequence but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment disclosed herein.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies disclosed herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological Characteristics of the Antibodies

In general, the antibodies of the present disclosure function by binding to GLP1R protein and decreasing its activity. For example, the present disclosure includes antibodies and antigen-binding fragments of antibodies that bind monomeric human GLP1R protein (e.g., at 25° C. or at 37° C.) with a $K_D$ of less than 20 nM as measured by surface plasmon resonance, e.g., using the assay format as defined in Example 3 herein. In certain embodiments, these antibodies or antigen-binding fragments thereof bind GLP1R with a $K_D$ of less than about 20 nM, less than about 18 nM, less than about 10 nM, less than about 7 nM, less than about 6 nM, less than about 5 nM, less than about 4 nM, less than about 3 nM, less than about 2 nM, less than about 1 nM, or less than about 0.5 nM, as measured by surface plasmon resonance at 25° C. or at 37° C., e.g., using the assay format as defined in Example 3 herein, or a substantially similar assay.

The present disclosure also includes antibodies and antigen-binding fragments of antibodies that bind monomeric cynomolgus GLP1R (e.g., at 25° C. or at 37° C.) with a $K_D$ of less than 60 nM as measured by surface plasmon resonance, e.g., using the assay format as defined in Example 3 herein. In certain embodiments, these antibodies or antigen-binding fragments thereof bind GLP1R with a $K_D$ of less than about 60 nM, less than about 20 nM, less than about 2 nM, less than about 1 nM, or less than about 0.5 nM, as measured by surface plasmon resonance at 25° C. or at 37° C., e.g., using the assay format as defined in Example 3 herein, or a substantially similar assay.

The present disclosure also includes antibodies and antigen-binding fragments of antibodies that bind hdesA-GLP1_GLP1R-MMH (e.g., at 25° C. or at 37° C.) with a $K_D$ of less than 75 nM as measured by surface plasmon resonance, e.g., using the assay format as defined in Example 3 herein. In certain embodiments, these antibodies or antigen-binding fragments thereof bind GLP1R with a $K_D$ of less than about 75 nM, less than about 70 nM, less than about 60 nM, less than about 40 nM, less than about 20 nM, or less than about 5 nM, as measured by surface plasmon resonance at 25° C. or at 37° C., e.g., using the assay format as defined in Example 3 herein, or a substantially similar assay.

The present disclosure also includes antibodies and antigen-binding fragments of antibodies that bind monomeric mouse GLP1R (e.g., at 25° C. or at 37° C.) with a $K_D$ of less than 75 nM as measured by surface plasmon resonance, e.g., using the assay format as defined in Example 3 herein. In certain embodiments, these antibodies or antigen-binding fragments thereof bind GLP1R with a $K_D$ of less than about 75 nM, less than about 50 nM, less than about 30 nM, less than about 20 nM, or less than about 11 nM, as measured by surface plasmon resonance at 25° C. or at 37° C., e.g., using the assay format as defined in Example 3 herein, or a substantially similar assay.

The present disclosure also includes antibodies and antigen-binding fragments thereof that block the interaction of GLP1 and GLP1R with an $IC_{50}$ value of less than about 10 nM as measured in an in vitro receptor/ligand binding assay at 37° C., as described in Example 4 herein. In certain embodiments, these antibodies or antigen-binding fragments thereof block the interaction of GLP1 and GLP1R with an $IC_{50}$ value of less than about 10 nM, less than about 7 nM, or less than about 2 nM, as measured in an in vitro receptor/ligand binding assay at 37° C., as described in Example 4 herein, or a substantially similar assay.

The present disclosure also includes antibodies and antigen-binding fragments of antibodies that bind to GLP1R and elevate blood glucose levels to reduce GLP1-induced hypoglycemia without causing hyperglycemia when administered to a subject in need thereof, e.g., as shown in Example 5 or 6 herein. In some embodiments, the antibodies and antigen-binding fragments of antibodies disclosed herein elevate blood glucose to a normalized level. In some embodiments, the antibodies and antigen-binding fragments of antibodies disclosed herein elevate blood glucose from a starting level below 55 mg/dL to a normalized level (e.g., above 70 mg/dL). In such embodiments, elevating blood glucose to a normalized level does not cause hyperglycemia.

The antibodies of the present disclosure may possess one or more of the aforementioned biological characteristics, or any combinations thereof. Other biological characteristics of the antibodies of the present disclosure will be evident to a person of ordinary skill in the art from a review of the present disclosure including the working Examples herein.

Epitope Mapping and Related Technologies

The present disclosure includes anti-GLP1R antagonist antibodies and antigen-binding fragments thereof, which interact with one or more amino acids found within one or more regions of the GLP1R protein molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the GLP1R protein molecule (e.g., a linear epitope in a domain). Alternatively, the epitope may consist of a plurality of non-contiguous amino acids (or amino acid sequences) located within either or both of the aforementioned domains of the protein molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) *Methods Mol. Biol.* 248:443-63), peptide cleavage analysis crystallographic studies and NMR analysis. In addition, methods such as epitope excision, epitope extraction and chemical modification of antigens can be employed (Tomer (2000) *Prot. Sci.* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267:252-259; Engen and Smith (2001) *Anal. Chem.* 73:256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

In certain embodiments, the present disclosure includes anti-GLP1R antibodies and antigen-binding fragments thereof that interact with one or more epitopes found within the extracellular domain of GLP1R. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular domain of GLP1R. Alternatively, the epitope may consist of a plurality of non-contiguous amino acids (or amino acid sequences) located within GLP1R.

The present disclosure includes anti-GLP1R antibodies that bind to the same epitope, or a portion of the epitope, as any of the specific exemplary antibodies listed in Table 1. Likewise, the present disclosure also includes anti-GLP1R antibodies that compete for binding to GLP1R protein or a fragment thereof with any of the specific exemplary antibodies listed in Table 1. For example, the present disclosure includes anti-GLP1R antibodies that cross-compete for binding to GLP1R protein with one or more antibodies listed in Table 1.

One can easily determine whether an antibody binds to the same epitope as, or competes for binding with, a reference anti-GLP1R antibody by using routine methods known in the art. For example, to determine if a test antibody binds to the same epitope as a reference anti-GLP1R antibody of the disclosure, the reference antibody is allowed to bind to a GLP1R protein or peptide under saturating conditions. Next, the ability of a test antibody to bind to the GLP1R protein molecule is assessed. If the test antibody is able to bind to GLP1R following saturation binding with the reference anti-GLP1R antibody, it can be concluded that the test antibody binds to a different epitope than the reference anti-GLP1R antibody. On the other hand, if the test antibody is not able to bind to the GLP1R protein following saturation binding with the reference anti-GLP1R antibody, then the test antibody may bind to the same epitope as the epitope bound by the reference anti-GLP1R antibody of the disclosure.

To determine if an antibody competes for binding with a reference anti-GLP1R antibody, the above-described binding methodology is performed in two orientations: In a first orientation, the reference antibody is allowed to bind to a GLP1R protein under saturating conditions followed by assessment of binding of the test antibody to the GLP1R molecule. In a second orientation, the test antibody is allowed to bind to a GLP1R molecule under saturating conditions followed by assessment of binding of the reference antibody to the GLP1R molecule. If, in both orientations, only the first (saturating) antibody is capable of binding to the GLP1R molecule, then it is concluded that the test antibody and the reference antibody compete for binding to GLP1R. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 1990, 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In certain embodiments, the present disclosure provides an isolated antibody or antigen-binding fragment thereof that binds specifically to GLP1R protein, wherein the antibody or antigen-binding fragment thereof interacts with one or more amino acids contained within the extracellular domain of GLP1R, as determined by hydrogen/deuterium exchange, and wherein the antibody or antigen-binding fragment thereof binds to and deactivates GLP1R.

Immunoconjugates

The present disclosure encompasses a human anti-GLP1R monoclonal antibody conjugated to a therapeutic moiety ("immunoconjugate"), to treat a GLP1R-associated disease or disorder (e.g., hypoglycemia). As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to GLP1R protein. The type of therapeutic moiety that may be conjugated to the anti-GLP1R antibody and will take into account the condition to be treated and the desired therapeutic effect to be achieved. Examples of suitable agents for forming immunoconjugates are known in the art. See, e.g., WO 05/103081.

Multi-Specific Antibodies

The antibodies of the present disclosure may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the disclosure, or variants thereof, may be constructed using standard molecular biological techniques (e.g., recombinant DNA and protein expression technology), as will be known to a person of ordinary skill in the art.

In some embodiments, GLP1R-specific antagonist antibodies are generated in a bi-specific format (a "bi-specific") in which variable regions binding to distinct domains of GLP1R protein are linked together to confer dual-domain specificity within a single binding molecule. Appropriately designed bi-specifics may enhance overall GLP1R-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific. See, e.g., US2011/0195454 and US2010/0331527.

Alternatively, antibodies that bind more than one domains and a second target, such as, but not limited to, for example, a second different anti-GLP1R antibody, may be prepared in a bi-specific format using techniques described herein, or other techniques known to those skilled in the art. Antibody variable regions binding to distinct regions may be linked together with variable regions that bind to relevant sites on, for example, the extracellular domain of GLP1R, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Other exemplary bi-specific formats that can be used in the context of the present disclosure include, without limitation, e.g., scFv-based or diabody bi-specific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bi-specific formats (see, e.g., Klein et al. 2012, mAbs 4:6, 1-11, and references cited therein, for a review of the foregoing formats). Bi-specific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. See, e.g., Kazane et al., *J. Am. Chem. Soc.* [Epub: Dec. 4, 2012].

Therapeutic Administration and Formulations

The present disclosure provides therapeutic compositions comprising the anti-GLP1R antagonist antibodies or antigen-binding fragments thereof of the present disclosure. Therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody or antigen-binding fragment thereof may vary depending upon the age and the size of a subject to be administered, target disease, conditions, route of administration, and the like. When an antibody or antigen-binding fragment thereof of the present disclosure is used for treating a disease or disorder in an adult patient, or for preventing such a disease, it is advantageous to administer the antibody or antigen-binding fragment thereof of the present disclosure normally at a single dose of about 0.1 to about 100 mg/kg body weight. Depending on the severity of the condition, the frequency and the duration of the treatment can be adjusted. In certain embodiments, the antibody or antigen-binding fragment thereof of the disclosure can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies and antigen-binding fragments thereof of the present disclosure is also contemplated herein. Antibody-conjugated nanoparticles may be used both for therapeutic and diagnostic applications. Antibody-conjugated nanoparticles and methods of preparation and use are described in detail by Arruebo et al., 2009, "Antibody-conjugated nanoparticles for biomedical applications," *J. Nanomat.*, Vol. 2009, Article ID 439389, 24 pages. Nanoparticles may be developed and conjugated to antibodies contained in pharmaceutical compositions to target cells. Nanoparticles for drug delivery have also been described in, for example, U.S. Pat. No. 8,257,740, or 8,246,995.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antibodies and antigen-binding fragments thereof of the present disclosure are useful for the treatment, and/or prevention of a disease or disorder or condition associated with GLP1R and/or for ameliorating at least one symptom associated with such disease, disorder or condition. In certain embodiments, an antibody or antigen-binding fragment thereof of the disclosure may be administered at a therapeutic dose to a patient with a disease, disorder or condition associated with GLP1R. Non-limiting examples of diseases, disorders, or conditions that may be treated, prevented, or alleviated using the antibodies and antigen-binding fragments thereof of the present disclosure include hypoglycemia of any origin, such as PBH or hypoglycemia resulting from other upper abdominal surgeries (e.g., esophagectomy, gastrectomy for stomach cancer and peptic ulcers), hyperinsulinism (e.g., congenital hyperinsulinism), recurrent hypoglycemia, postprandial hypoglycemia, insulin hypersecretion in patients with recurrent hypoglycemia after gastric bypass, and hypoglycemia as a symptom of late dumping syndrome.

Hypoglycemia (e.g., PBH) is a disorder that is characterized by low blood sugar with or without elevated insulin levels. In PBH, hypoglycemia typically occur in subjects 1-3 hours after meals. Mild to moderate hypoglycemia manifests as hypoglycemic symptoms confirmed by blood glucose concentrations of <70 mg/dL. Severe hypoglycemia manifests as neuroglycopenic symptoms confirmed by blood glucose concentrations of <55 mg/dL. Neuroglycopenic symptoms may include confusion, loss of focus, fatigue, ataxia, paralysis, seizures, or loss of consciousness. Other symptoms, such as vasomotor symptoms (e.g., sweating and shakiness), and/or adrengeric symptoms (e.g., heart palpitations) may occur in hypoglycemic subjects as well.

In certain embodiments, the antibodies and antigen-binding fragments thereof of the present disclosure are useful for treating, alleviating, or preventing hypoglycemia, such as PBH or hypoglycemia resulting from other upper abdominal surgeries such as esophagectomy, gastrectomy for stomach cancer and peptic ulcers, and the like, or hypoglycemia resulting from inherent etiologies such as genetic abnormalities). It is also contemplated herein to use one or more antibodies of the present disclosure prophylactically to subjects at risk for suffering from low glucose levels or hypoglycemia.

In one embodiment, the present antibodies and antigen-binding fragments thereof are used for the preparation of a pharmaceutical composition or medicament for treating patients suffering from a disease, disorder or condition disclosed herein (e.g., low glucose levels or hypoglycemia). In another embodiment, the present antibodies and antigen-binding fragments thereof are used as adjunct therapy with any other agent or any other therapy known to those skilled in the art useful for treating or ameliorating a disease, disorder or condition disclosed herein (e.g., low glucose levels or hypoglycemia).

EXAMPLES

The following examples are put forth so as to provide those of ordinary skill in the art with a complete disclosure and description of how to make and use the methods and compositions of the present disclosure and are not intended to limit the scope of what the inventors regard as their invention. Likewise, the disclosure is not limited to any particular preferred embodiments described herein. Indeed, modifications and variations of the embodiments may be apparent to those skilled in the art upon reading this specification and can be made without departing from its spirit and scope. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Glucagon-Like Peptide Receptor 1 (GLP1R)

Human antibodies to GLP1R protein were generated in a VELOCIMMUNE® mouse comprising DNA encoding human Immunoglobulin heavy and kappa light chain variable regions. The mice were immunized with a stabilized full-length GLP1R protein.

The antibody immune response was monitored by a GLP1R-specific immunoassay. When a desired immune response was achieved, splenocytes were harvested and fused with mouse myeloma cells to preserve their viability and form hybridoma cell lines. The hybridoma cell lines were screened and selected to identify cell lines that produce GLP1R-specific antibodies. The cell lines were used to obtain several anti-GLP1R chimeric antibodies (i.e., antibodies possessing human variable domains and mouse constant domains).

Anti-GLP1R antibodies were also isolated directly from antigen-positive mouse B cells (described in U.S. 2007/0280945A1). Using this method, several fully human anti-GLP1R antibodies (i.e., antibodies possessing human variable domains and human constant domains) were obtained.

Exemplary antibodies generated as disclosed above were designated as mAb36986, mAb37639, and mAb37645. The biological properties of the exemplary antibodies generated in accordance with the methods of this Example are further described in the Examples below.

Example 2: Heavy and Light Chain Variable Region Amino Acid and Nucleotide Sequences Table 1 sets forth the amino acid sequence identifiers of the heavy and light chain variable regions and CDRs of selected anti-GLP1R antagonist antibodies of the present disclosure.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| mAb36986 | 2 | 4 | 6 | 8 | 10 | 12 | 14 | 16 |
| mAb37639 | 22 | 24 | 26 | 28 | 30 | 32 | 14 | 34 |
| mAb37645 | 40 | 42 | 44 | 46 | 48 | 50 | 52 | 54 |

The corresponding nucleic acid sequence identifiers are set forth in Table 2.

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb36986 | 1 | 3 | 5 | 7 | 9 | 11 | 13 | 15 |
| mAb37639 | 21 | 23 | 25 | 27 | 29 | 31 | 13 | 33 |
| mAb37645 | 39 | 41 | 43 | 45 | 47 | 49 | 51 | 53 |

Antibodies referred to herein typically have fully human variable regions but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain. In certain embodiments, selected antibodies with a mouse IgG1 Fc are converted to antibodies with human IgG4 Fc.

Table 3 sets forth the amino acid sequence identifiers of heavy chain and light chain sequences of selected anti-GLP1R antibodies with human IgG4 Fc.

TABLE 3

Amino Acid Sequence Identifiers

| Antibody Designation | SEQ ID NOs: | |
|---|---|---|
| | Heavy Chain | Light Chain |
| mAb36986 | 18 | 20 |
| mAb37639 | 36 | 38 |
| mAb37645 | 56 | 58 |

Example 3: GLP1R Monoclonal Antibody Binding to GLP1R as Determined by Surface Plasmon Resonance at 25° C. and 37° C.

The equilibrium dissociation constant ($K_D$) for GLP1R binding to selected GLP1R monoclonal antibodies (mAbs) was determined using a real-time surface plasmon resonance biosensor using a Biacore 4000 instrument. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with human Fc specific mouse mAb to capture different GLP1R mAbs. Different concentrations (100, 25, and 6.25 nM) of the N-terminal region of human GLP1R-MMH (hGLP1R-MMH; SEQ ID NO: 59), human GLP1R expressed with mouse IgG2a Fc (hGLP1R-mFc; SEQ ID NO: 63), an in-line fusion protein of human desA-GLP1 and GLP1R-MMH (hdesA-GLP1_GLP1R-MMH; SEQ ID NO: 62), Macaca fascicularis GLP1R-MMH (mfGLP1R-MMH; SEQ ID NO: 60) or 100 nM mouse GLP1R-MMH (mGLP1R-MMH; SEQ ID NO: 61) prepared in HBS-ET running buffer were injected over the GLP1R mAb captured surface for 150 sec at a flow rate of 30 μL/min and their dissociation in HBS-ET running buffer was monitored for 10 minutes. At the end of each cycle, the GLP1R mAb capture surface was regenerated using a 12 sec injection of 20 mM phosphoric acid.

The association rate ($k_a$) and dissociation rate ($K_d$) were determined by fitting the real-time binding sensorgrams to a 1:1 binding model with mass transport limitation using Scrubber 2.0 c curve-fitting software. Binding dissociation equilibrium constant ($K_D$) and dissociative half-life (t½) were calculated from the kinetic rates as:

$$K_D(M) = \frac{kd}{ka}, \text{ and}$$

$$t\frac{1}{2}(\min) = \frac{\ln(2)}{60 * kd}$$

Binding kinetics parameters for GLP1R binding to selected GLP1R mAbs at 25° C. and 37° C. are shown in Tables 4 through 13.

TABLE 4

Binding kinetics parameters of selected GLP1R monoclonal antibodies (mAbs) binding to hGLP1R-MMH at 25° C.

| mAb Captured | mAb Capture Level (RU) | 100 nM hGLP1R-MMH Bound (RU) | $k_a$ (1/Ms) | $k_d$ (1/s) | $K_D$ (M) | t½ (min) |
|---|---|---|---|---|---|---|
| mAb36986 | 350 ± 3.3 | 115 | 7.17E+05 | 9.97E−05 | 1.39E−10 | 116 |
| mAb37639 | 332 ± 2.1 | 103 | 3.93E+05 | 1.86E−04 | 4.74E−10 | 62 |
| mAb37645 | 246 ± 0.5 | 60 | 1.52E+05 | 8.66E−04 | 5.72E−09 | 13 |

TABLE 5

Binding kinetics parameters of selected GLP1R monoclonal antibodies (mAbs) binding to hGLP1R-MMH at 37° C.

| mAb Captured | mAb Capture Level (RU) | 100 nM hGLP1R-MMH Bound (RU) | $k_a$ (1/Ms) | $k_d$ (1/s) | $K_D$ (M) | t½ (min) |
|---|---|---|---|---|---|---|
| mAb36986 | 415 ± 5.2 | 135 | 9.15E+05 | 5.44E−04 | 5.94E−10 | 21 |
| mAb37639 | 388 ± 1.8 | 123 | 6.68E+05 | 4.22E−04 | 6.32E−10 | 27 |
| mAb37645 | 298 ± 1.3 | 70 | 1.95E+05 | 3.49E−03 | 1.80E−08 | 3.3 |

TABLE 6

Binding kinetics parameters of selected GLP1R monoclonal antibodies (mAbs) binding to hGLP1R-mFc at 25° C.

| mAb Captured | mAb Capture Level (RU) | 100 nM hGLP1R-mFc Bound (RU) | $k_a$ (1/Ms) | $k_d$ (1/s) | $K_D$ (M) | t½ (min) |
|---|---|---|---|---|---|---|
| mAb36986 | 345 ± 0.8 | 187 | 1.04E+05 | 7.64E−05 | 7.35E−10 | 151 |
| mAb37639 | 331 ± 0.8 | 122 | 6.59E+04 | 1.56E−04 | 2.37E−09 | 74 |
| mAb37645 | 245 ± 0.6 | 91 | 1.28E+05 | 1.83E−04 | 1.42E−09 | 63 |

TABLE 7

Binding kinetics parameters of selected GLP1R monoclonal antibodies (mAbs) binding to hGLP1R-mFc at 37° C.

| mAb Captured | mAb Capture Level (RU) | 100 nM hGLP1R-mFc Bound (RU) | $k_a$ (1/Ms) | $k_d$ (1/s) | $K_D$ (M) | t½ (min) |
|---|---|---|---|---|---|---|
| mAb36986 | 405 ± 2 | 246 | 1.29E+05 | 4.32E−04 | 3.35E−09 | 27 |
| mAb37639 | 384 ± 0.6 | 185 | 1.01E+05 | 3.54E−04 | 3.52E−09 | 33 |
| mAb37645 | 297 ± 1.3 | 116 | 2.51E+05 | 6.50E−04 | 2.59E−09 | 18 |

TABLE 8

Binding kinetics parameters of selected GLP1R monoclonal antibodies (mAbs) binding to mfGLP1R-MMH at 25° C.

| mAb Captured | mAb Capture Level (RU) | 100 nM mfGLP1R-MMH Bound (RU) | $k_a$ (1/Ms) | $k_d$ (1/s) | $K_D$ (M) | t½ (min) |
|---|---|---|---|---|---|---|
| mAb36986 | 347 ± 1.3 | 103 | 2.40E+05 | 1.02E−04 | 4.24E−10 | 113 |
| mAb37639 | 331 ± 1.2 | 83 | 1.37E+05 | 1.95E−04 | 1.42E−09 | 59 |
| mAb37645 | 246 ± 0.8 | 35 | 4.22E+04 | 8.26E−04 | 1.96E−08 | 14 |

TABLE 9

Binding kinetics parameters of selected GLP1R monoclonal antibodies (mAbs) binding to mfGLP1R-MMH at 37° C.

| mAb Captured | mAb Capture Level (RU) | 100 nM mfGLP1R-MMH Bound (RU) | $k_a$ (1/Ms) | $k_d$ (1/s) | $K_D$ (M) | t½ (min) |
|---|---|---|---|---|---|---|
| mAb36986 | 407 ± 2.2 | 128 | 3.15E+05 | 5.01E−04 | 1.59E−09 | 23 |
| mAb37639 | 385 ± 0.7 | 110 | 2.15E+05 | 4.18E−04 | 1.94E−09 | 28 |
| mAb37645 | 298 ± 1.8 | 42 | 6.95E+04 | 3.84E−03 | 5.52E−08 | 3.0 |

TABLE 10

Binding kinetics parameters of selected GLP1R monoclonal antibodies (mAbs) binding to hdesA-GLP1_GLP1R-MMH at 25° C.

| mAb Captured | mAb Capture Level (RU) | 100 nM hdesA-GLP1_GLP1R-MMH Bound (RU) | $k_a$ (1/Ms) | $k_d$ (1/s) | $K_D$ (M) | $t\frac{1}{2}$ (min) |
|---|---|---|---|---|---|---|
| mAb36986 | 347 ± 0.6 | 13 | 3.04E+04 | 1.08E−04 | 3.56E−09 | 107 |
| mAb37639 | 331 ± 0.5 | 8  | 1.19E+04 | 1.90E−04 | 1.60E−08 | 61 |
| mAb37645 | 245 ± 0.6 | 58 | 1.20E+05 | 5.20E−04 | 4.32E−09 | 22 |

TABLE 11

Binding kinetics parameters of selected GLP1R monoclonal antibodies (mAbs) binding to hdesA-GLP1_GLP1R-MMH at 37° C.

| mAb Captured | mAb Capture Level (RU) | 100 nM hdesA-GLP1_GLP1R-MMH Bound (RU) | $k_a$ (1/Ms) | $k_d$ (1/s) | $K_D$ (M) | $t\frac{1}{2}$ (min) |
|---|---|---|---|---|---|---|
| mAb36986 | 410 ± 0.4 | 28 | 1.63E+04 | 9.87E−04 | 6.04E−08 | 12 |
| mAb37639 | 386 ± 1.1 | 21 | 1.71E+04 | 1.27E−03 | 7.42E−08 | 9 |
| mAb37645 | 297 ± 0.6 | 71 | 1.39E+05 | 2.29E−03 | 1.65E−08 | 5.0 |

TABLE 12

Binding kinetics parameters of selected GLP1R monoclonal antibodies (mAbs) binding to mGLP1R-MMH at 25° C.

| mAb Captured | mAb Capture Level (RU) | 100 nM mGLP1R-MMH Bound (RU) | $k_a$ (1/Ms) | $k_d$ (1/s) | $K_D$ (M) | $t\frac{1}{2}$ (min) |
|---|---|---|---|---|---|---|
| mAb36986 | 345 ± 0.6 | 88 | 4.49E+05 | 9.02E−03 | 2.01E−08 | 1.3 |
| mAb37639 | 330 ± 0.8 | 85 | 2.69E+05 | 4.54E−03 | 1.69E−08 | 2.5 |
| mAb37645 | 244 ± 0.3 | 30 | 5.69E+04 | 6.17E−04 | 1.08E−08 | 19 |

TABLE 13

Binding kinetics parameters of selected GLP1R monoclonal antibodies (mAbs) binding to mGLP1R-MMH at 37° C.

| mAb Captured | mAb Capture Level (RU) | 100 nM mGLP1R-MMH Bound (RU) | $k_a$ (1/Ms) | $k_d$ (1/s) | $K_D$ (M) | $t\frac{1}{2}$ (min) |
|---|---|---|---|---|---|---|
| mAb36986 | 405 ± 0.8 | 70 | 6.49E+05 | 4.85E−02 | 7.47E−08 | 0.24 |
| mAb37639 | 383 ± 0.2 | 97 | 4.35E+05 | 9.59E−03 | 2.21E−08 | 1.2 |
| mAb37645 | 296 ± 0   | 42 | 8.36E+04 | 2.49E−03 | 2.98E−08 | 4.6 |

Example 4: Functional Inhibition of Human GLP1R

This example relates to functional inhibition of human GLP1R in a cell-based bioassay with HEK293/FSC11/pCDNA3.1+GLP1R+1 nM GLP1 cells, activated by hGLP1, using the following anti-GLP1R antagonist antibodies: mAb36986, mAb37639, and mAb37645.

GLP1R is a member of the secretin family (Class B) of G protein-coupled receptors (GPCRs). Upon binding of its ligand, GLP1, GLP1R initiates a downstream signaling cascade through Gαs G-proteins that raises intracellular cyclic AMP (cAMP) levels, which leads to the transcriptional regulation of genes (Donnelly, Br J Pharmacol, 166(1):27-41 (2011)). To assess anti-hGLP1R antibody inhibition of GLP1R, a bioassay was established in HEK293 cells (human embryonic kidney 293, ATCC) transfected to stably express a reporter gene [cAMP response element (4x)-luciferase-IRES-GFP] along with a full-length human GLP1R. The resulting cell line was named HEK293/FSC11/pCDNA3.1+GLP1R+1 nM GLP (ACL #6822, Regeneron), and is henceforth referred to as HEK293/CRE-luc/GLP1R.

For the bioassay, HEK293/CRE-luc/GLP1R cells were plated at 20,000 cells per well in assay media (Opti-MEM media containing 0.1% fetal bovine serum and 1× Penicillin-Streptomycin-Glutamine) and incubated overnight at 37° C. in 5% $CO_2$. The following day, selected anti-GLP1R antibodies or an isotype control antibody were serially diluted in assay media 1:3 from 300 nM to 5.08 µM (with an additional well for assay media alone without test molecule) and pre-incubated with HEK293/CRE-luc/GLP1R cells for 30 minutes at 37° C. in 5% $CO_2$. Exendin-3 (9-39) amide (Tocris, cat. #2081), referred to hereafter as Exendin-9, was serially diluted in assay media 1:3 from 500 nM to 8.47 pM (with an additional well without test molecule) and pre-incubated with the cells for 30 minutes at 37° C. in 5% $CO_2$. After 30 minutes, GLP-1 (7-36) amide (Phoenix Pharmaceuticals, cat #028-11), referred to hereafter as GLP1, was added to the cells at a constant concentration of 40 pM in assay media. GLP1 was also serially diluted in assay media 1:3 from 100 nM to 1.69 pM (with an additional well without test molecule) and added to cells not treated with the antibodies or Exendin-9 for a dose response of the ligand. After a 5 hour incubation at 37° C. in 5% $CO_2$, luciferase activity was evaluated by the addition of ONEGLO™ luciferase assay system reagent (Promega, cat. #E6130) and Relative Luminescence Units (RLU) were measured using an Envision Plate reader (Perkin Elmer). Results were analyzed using a nonlinear regression (4-parameter logistic) in PRISM® 7 software to obtain $EC_{50}$ and $IC_{50}$ values. The percent inhibition was calculated using the following equation:

$$\% \; Inhibition = 100 \times \frac{RLU_{GLP1} - RLU_{inhibition}}{RLU_{GLP1} - RLU_{no \; GLP1 \; control}}$$

In the above equation, "$RLU_{GLP1}$" refers to the relative luminescence unit (RLU) value from cells treated with 40 pM GLP1 without antibodies. "$RLU_{inhibition}$" refers to the lowest RLU value measured at the maximum antibody or Exendin-9 dose response concentration with 40 pM GLP1. "$RLU_{no \; GLP1 \; control}$" refers to RLU value of the cells measured in the absence of GLP1, Exendin-9 or antibodies.

Results: Three anti-GLP1R antibodies were tested for inhibition of HEK293/CRE-luc/GLP1R cells activated with 40 pM GLP1. As shown in Table 14, two anti-GLP1R antibodies, mAb36986 and mAb37639, showed 100% inhibition with $IC_{50}$ values of 1.69 nM and 6.55 nM, respectively. mAb37645 inhibited GLP1R activation by 73% with an $IC_{50}$ value of 1.23 nM. The isotype control mAb showed no inhibition. Exendin-9 showed 100% inhibition with an $IC_{50}$ of 29.4 nM. GLP1 activated cells with an $EC_{50}$ value of 44.6 pM.

TABLE 14

Anti-GLP1R antibody inhibition of human GLP1R activation on HEK293/CRE-luc/GLP1R cells by 40 pM GLP1.
GLP1 $EC_{50}$ [M] = 4.46E−11

| Antibody or Peptide | % Inhibition | IC50 [M] |
| --- | --- | --- |
| mAb36986 | 100 | 1.69E−09 |
| mAb37639 | 100 | 6.55E−09 |
| mAb37645 | 73 | 1.23E−09 |
| Isotype Control mAb | no inhibition | no inhibition |
| Exendin-9 | 100 | 2.94E−08 |

Example 5: Effect of GLP1R Antagonist Antibodies on Exendin-4 Induced Hypoglycemia in GLP1R Humanized Mice This example relates to an in vivo study using the following anti-GLP1R antagonist antibodies: mAb36986, mAb37639, and mAb37645.

To determine glucose elevating effects of anti-GLP1R antagonist antibodies on GLP1-induced hypoglycemia, 6-month-old male mice homozygous for the expression of human GLP1R in place of mouse GLP1R (referred to as GLP1R humanized mice) were administered once with selected anti-GLP1R antibodies and periodically challenged by a GLP1 analogue, Exendin-4 (Sigma, cat #E7144), for the next 67 days.

For the study, 35 mice were randomly divided into one group of fourteen mice and three groups of seven mice. On Day 0, the group of fourteen animals (later divided into Groups 1 and 2) were administered subcutaneously (s.c.) with a mIgG2 isotype control antibody (referred to as Isotype control, dose of 25 mg/kg), whereas the other three groups (n=7/group) were each administered s.c. (dose of 25 mg/kg) with mAb36986 (Group 3), mAb37639 (Group 4), or mAb37645 (Group 5). The next day (Day 1), the isotype control administered fourteen animals were randomly divided into two groups (Group 1 and 2) of seven mice each. At 0 minute on Day 1, animals in Group 1 were administered intraperitoneally (i.p.) with saline, whereas animals in Group 2 were administered i.p. with Exendin-4 (dose of 0.01 mg/kg). At the same time point, animals in Groups 3, 4, and 5 were administered i.p. with Exendin-4 (dose of 0.01 mg/kg). For all animals, blood glucose levels were measured with a handheld glucometer immediately before saline or Exendin-4 administration, and 15, 30, 60, and 120 minutes post administration. All animals remained in their assigned groups until the study completion on Day 67. The Exendin-4 challenge performed on Day 1 was repeated on Days 8, 22, 46, and 67. Mean±SEM of blood glucose levels at each time point was calculated for each group and shown in Table 15. Mean±SEM of percent differences in blood glucose levels from Group 1 at each time point was calculated for each group and shown in Table 16. Statistical analyses were performed by two-way ANOVA followed by Bonferroni post-hoc tests, comparing Groups 2, 3, 4, and 5 to Group 1.

Animals administered with isotype control on Day 0 and saline on days of Exendin-4 challenge (Group 1) showed injection-related elevation in blood glucose levels at early time points (i.e., 15, 30, and 60 minutes) consistently on Days 1, 8, 22, 46, and 67. Animals administered with isotype control on Day 0 and Exendin-4 on days of Exendin-4 challenge (Group 2) showed Exendin-4 induced reductions in blood glucose levels on each day the challenge was performed. Animals administered with mAb36986 on Day 0 and Exendin-4 on Days 1, 8, 22, 46, and 67 (Group 3) showed glucose levels similar to the level measured from Group 1 at every time point on each day when Exendin-4 challenge was performed with exception of the last day (Day 67). The data demonstrates that a single, high dose mAb36986 can correct GLP1-induced hypoglycemia at least for 46 days in mice. There were no differences in blood glucose levels between Groups 1 and 3 at 0 minute time point on each day the challenge was performed. The data exhibit that mAb36986 does not cause hyperglycemia in mice under the conditions tested.

As shown in FIG. 1, animals administered with mAb37639 on Day 0 and Exendin-4 on Days 1, 8, 22, 46, and 67 (Group 4) showed glucose normalizing effects only on Days 1 and 8, indicating that mAb37639 has shorter duration of action compared to mAb36986. Animals administered with mAb37645 on Day 0 and Exendin-4 on Days 1, 8, 22, 46, and 67 (Group 5) did not exhibit glucose normalizing effects. Additionally, mAb36986 was shown to be long-acting and also corrected GLP1-induced hypoglycemia without causing hyperglycemia in mice.

TABLE 15

Blood glucose levels (mg/dL) during exendin-4 challenges performed on 1, 8, 22, 46 and 67 days post antibody administration

| | | Group | | | | | | | | | |
|---|---|---|---|---|---|---|---|---|---|---|---|
| | | 1 | | 2 | | 3 | | 4 | | 5 | |
| | | Antibody dosed on Day 0 | | | | | | | | | |
| | | Isotype control | | Isotype control | | mAb37639 | | mAb37645 | | mAb36986 | |
| | | | | Administration on Days 1, 8, 22, 46, and 67 | | | | | | | |
| | | Saline | | Exendin-4 | | Exendin-4 | | Exendin-4 | | Exendin-4 | |
| Day | Min | Mean | SEM | Mean | SEM | Mean | SEM | Mean | SEM | Mean | SEM |
| 1 | 0 | 192 | 10 | 199 | 7 | 215 | 7 | 216 | 9 | 214 | 12 |
| | 15 | 255 | 17 | 139**** | 7 | 233 | 8 | 195** | 16 | 248 | 16 |
| | 30 | 254 | 14 | 126**** | 7 | 222 | 11 | 151**** | 11 | 252 | 17 |
| | 60 | 233 | 17 | 124**** | 9 | 226 | 8 | 140**** | 7 | 225 | 15 |
| | 120 | 223 | 15 | 152*** | 9 | 212 | 7 | 160** | 11 | 218 | 13 |
| 8 | 0 | 212 | 11 | 206 | 7 | 214 | 17 | 204 | 7 | 196 | 13 |
| | 15 | 258 | 17 | 124**** | 8 | 223 | 11 | 182*** | 12 | 238 | 7 |
| | 30 | 246 | 28 | 114**** | 6 | 216 | 13 | 158**** | 17 | 245 | 10 |
| | 60 | 242 | 18 | 122**** | 9 | 221 | 11 | 146**** | 14 | 242 | 12 |
| | 120 | 210 | 19 | 144** | 19 | 215 | 7 | 182 | 9 | 199 | 9 |
| 22 | 0 | 210 | 14 | 190 | 9 | 199 | 9 | 192 | 10 | 207 | 3 |
| | 15 | 266 | 19 | 136**** | 13 | 216* | 8 | 149**** | 13 | 251 | 12 |
| | 30 | 252 | 11 | 117**** | 14 | 199** | 16 | 121**** | 8 | 232 | 4 |
| | 60 | 239 | 19 | 122**** | 6 | 188* | 12 | 139**** | 15 | 229 | 8 |
| | 120 | 208 | 8 | 146*** | 6 | 203 | 11 | 167 | 17 | 219 | 8 |
| 46 | 0 | 183 | 11 | 173 | 4 | 185 | 9 | 184 | 11 | 180 | 10 |
| | 15 | 245 | 18 | 126**** | 12 | 184** | 15 | 167*** | 18 | 237 | 20 |
| | 30 | 250 | 19 | 112**** | 4 | 171*** | 8 | 138**** | 10 | 224 | 25 |
| | 60 | 227 | 12 | 124**** | 9 | 165** | 7 | 144**** | 18 | 222 | 16 |
| | 120 | 186 | 11 | 147 | 12 | 199 | 12 | 184 | 11 | 206 | 10 |
| 67 | 0 | 195 | 15 | 183 | 12 | 196 | 17 | 195 | 16 | 199 | 12 |
| | 15 | 265 | 19 | 136**** | 18 | 165**** | 17 | 153**** | 21 | 210* | 15 |
| | 30 | 262 | 16 | 123**** | 5 | 146**** | 19 | 144**** | 22 | 144**** | 8 |
| | 60 | 237 | 8 | 122**** | 8 | 149*** | 11 | 144**** | 24 | 155*** | 7 |
| | 120 | 226 | 8 | 164* | 8 | 186 | 8 | 168* | 20 | 190 | 12 |

*P < 0.05,
**P < 0.01,
***P < 0.001,
****P < 0.0001, compared to Group 1.

TABLE 16

Percent differences in blood glucose levels from Group 1 during Exendin-4 challenges performed on 1, 8, 22, 46 and 67 days post antibody administration

| | | Group | | | | | | | | | |
|---|---|---|---|---|---|---|---|---|---|---|---|
| | | 1 | | 2 | | 3 | | 4 | | 5 | |
| | | Antibody dosed on Day 0 | | | | | | | | | |
| | | Isotype control | | Isotype control | | mAb37639 | | mAb37645 | | mAb36986 | |
| | | | | Administration on Days 1, 8, 22, 46, and 67 | | | | | | | |
| | | Saline | | Exendin-4 | | Exendin-4 | | Exendin-4 | | Exendin-4 | |
| Day | Min | Mean | SEM | Mean | SEM | Mean | SEM | Mean | SEM | Mean | SEM |
| 1 | 0 | 0 | 5 | 4 | 4 | 12 | 4 | 13 | 5 | 11 | 6 |
| | 15 | 0 | 7 | −46**** | 3 | −9 | 3 | −24** | 6 | −3 | 6 |
| | 30 | 0 | 6 | −50**** | 3 | −13 | 4 | −41**** | 5 | −1 | 7 |
| | 60 | 0 | 7 | −47**** | 4 | −6 | 5 | −38**** | 5 | −4 | 7 |
| | 120 | 0 | 7 | −32*** | 4 | −7 | 4 | −26** | 5 | −2 | 6 |
| 8 | 0 | 0 | 5 | −3 | 3 | 1 | 8 | −8 | 3 | −8 | 6 |
| | 15 | 0 | 7 | −52**** | 3 | −13 | 4 | −30** | 4 | −8 | 3 |
| | 30 | 0 | 11 | −53**** | 2 | −12 | 5 | −36*** | 7 | 0 | 4 |
| | 60 | 0 | 8 | −50**** | 4 | −9 | 4 | −40**** | 6 | 0 | 5 |
| | 120 | 0 | 9 | −31*** | 9 | 2 | 3 | −13 | 4 | −5 | 4 |
| 22 | 0 | 0 | 6 | −9 | 4 | −5 | 4 | −8 | 5 | −1 | 2 |
| | 15 | 0 | 7 | −49**** | 5 | −19* | 3 | −44**** | 5 | −6 | 4 |

TABLE 16-continued

Percent differences in blood glucose levels from Group 1 during
Exendin-4 challenges performed on 1, 8, 22, 46 and 67 days post antibody administration

| | | Group | | | | | | | | | |
|---|---|---|---|---|---|---|---|---|---|---|---|
| | | 1 | | 2 | | 3 | | 4 | | 5 | |
| | | \multicolumn{10}{c}{Antibody dosed on Day 0} | | | | | | | | | |
| | | Isotype control | | Isotype control | | mAb37639 | | mAb37645 | | mAb36986 | |
| | | | | \multicolumn{8}{c}{Administration on Days 1, 8, 22, 46, and 67} | | | | | | | | |
| | | Saline | | Exendin-4 | | Exendin-4 | | Exendin-4 | | Exendin-4 | |
| Day | Min | Mean | SEM | Mean | SEM | Mean | SEM | Mean | SEM | Mean | SEM |
| | 30 | 0 | 5 | −53**** | 6 | −21* | 6 | −52**** | 3 | −8 | 2 |
| | 60 | 0 | 8 | −49**** | 3 | −21* | 5 | −42**** | 6 | −4 | 3 |
| | 120 | 0 | 4 | −30*** | 3 | −2 | 5 | −20* | 8 | 5 | 4 |
| 46 | 0 | 0 | 6 | −19 | 14 | 1 | 5 | 1 | 6 | −2 | 6 |
| | 15 | 0 | 7 | −56**** | 8 | −25 | 6 | −32** | 7 | −3 | 8 |
| | 30 | 0 | 8 | −62**** | 7 | −32** | 3 | −45*** | 4 | −10 | 10 |
| | 60 | 0 | 5 | −53**** | 9 | −27* | 3 | −36** | 8 | −2 | 7 |
| | 120 | 0 | 6 | −32** | 13 | 7 | 7 | −1 | 6 | 11 | 5 |
| 67 | 0 | 0 | 8 | −20 | 14 | 1 | 9 | 0 | 8 | 2 | 6 |
| | 15 | 0 | 7 | −56**** | 9 | −38** | 7 | −42*** | 8 | −21 | 6 |
| | 30 | 0 | 6 | −60**** | 7 | −44*** | 7 | −45*** | 9 | −45*** | 3 |
| | 60 | 0 | 3 | −56**** | 8 | −37** | 5 | −39** | 10 | −34** | 3 |
| | 120 | 0 | 4 | −38** | 11 | −18 | 4 | −26 | 9 | −16 | 5 |

*P < 0.05,
**P < 0.01,
***P < 0.001,
****P < 0.0001, compared to Group 1.

Example 6: Effect of a GLP1R Antagonist Antibody on GLP1-Induced Hypoglycemia in GLP1R Humanized Mice This example relates to a study conducted to determine the glucose elevating efficacy and duration of action of an anti-GLP1R antagonist antibody, mAb36986, on GLP1-induced hypoglycemia. Mice homozygous for the expression of human GLP1R in place of mouse GLP1R (referred to as GLP1R humanized mice) were administered with mAb36986 and repeatedly challenged by a GLP1 analogue, Exendin-4 (Sigma, cat #E7144). The efficacy and duration of action of mAb36986 was compared to a peptide GLP1R antagonist, Exendin (9-39) (Bachem, cat #4017799), referred to hereafter as Exendin-9, in this example.

Thirty-nine, 2.5-month-old male GLP1R humanized mice were randomly divided into one group of sixteen mice, two groups of eight mice, and one group of seven mice. On Day 0, the group of sixteen animals (Groups 1 and 2) were administered subcutaneously (s.c.) with a hIgG4 isotype control antibody (referred to as isotype control, dose of 10 mg/kg). One group of eight animals (Group 3) was administered s.c. with Exendin-9 (dose of 10 mg/kg), whereas the other group of eight animals (Group 4) was administered s.c. (dose of 3 mg/kg) with mAb36986. The group of seven animals (Group 5) was administered s.c. (dose of 10 mg/kg) with mAb36986. The next day (Day 1), the isotype control administered animals were randomly divided into two groups (Group 1 and 2) of eight mice. Twenty-four hours post test article administration (=0-minute timepoint on Day 1), animals in Group 1 were administered intraperitoneally (i.p.) with saline, whereas animals in Group 2 were administered i.p. with Exendin-4 (dose of 0.01 mg/kg). At the same time point, animals in Groups 3, 4, and 5 were administered i.p. with Exendin-4 (dose of 0.01 mg/kg). For all animals, blood glucose levels were measured with a handheld glucometer immediately before and 15, 30, 60, and 120 minutes after saline or Exendin-4 administration. All animals remained in their assigned groups until the study completion on Day 80. With animals in Groups 1, 2, 4, and 5, the Exendin-4 challenge was repeated on Days 3, 7, 15, 21, 29, 65, and 80. With animals in Group 3, another dose of Exendin-9 was administered on Day 3 and the Exendin-4 challenge was performed 0.5 and 4.5 hours post Exendin-9 administration.

Figure 2:
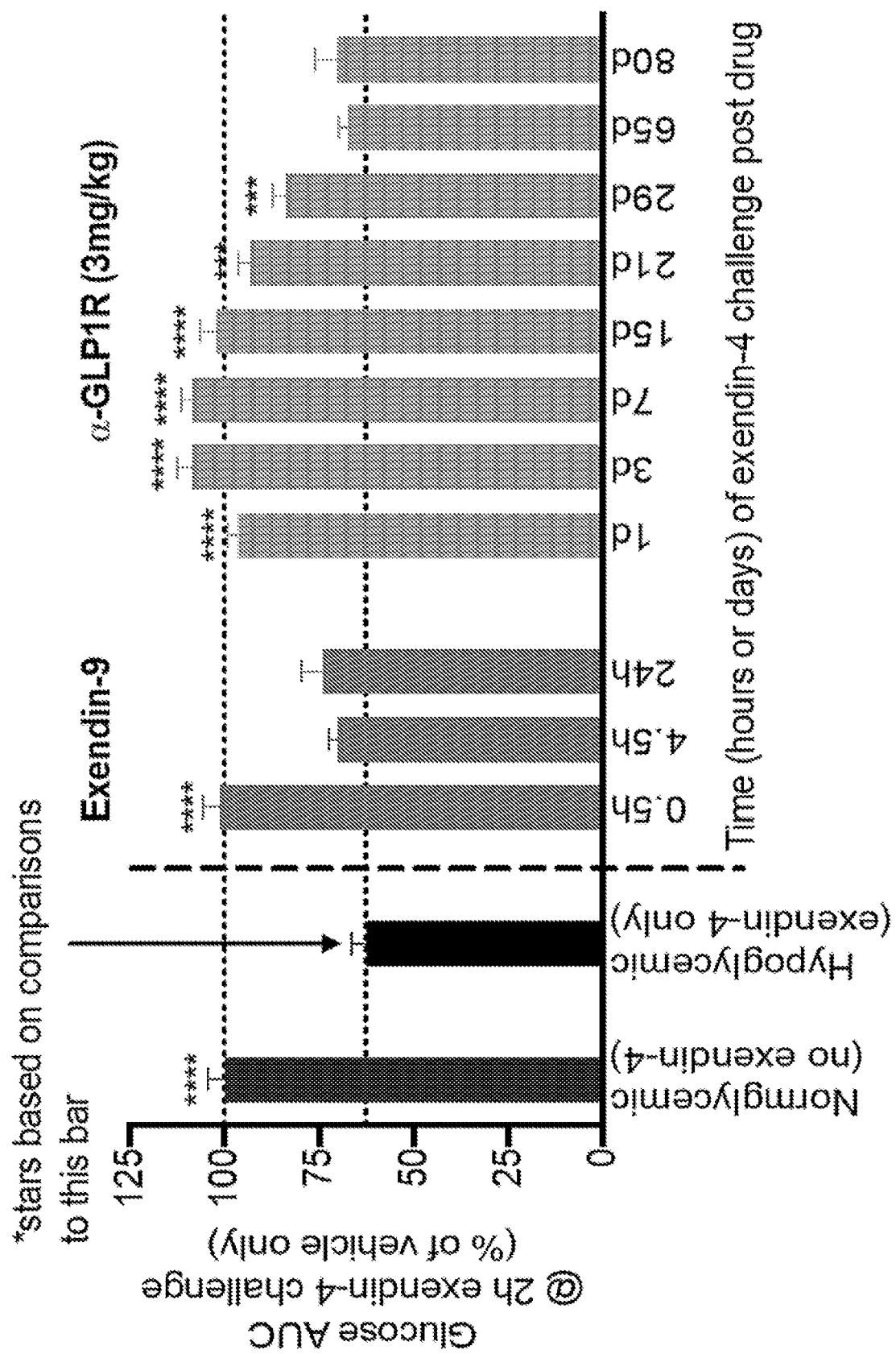
FIG. 2 is a graph showing area under the curve (AUC) of blood glucose levels in mice treated with an anti-GLP1R antibody of the present disclosure or with Exendin-9 upon challenge with Exendin-4, as described in Example 6 herein.

For each Exendin-4 challenge, area under the curve (AUC) of blood glucose levels during the 120-minute challenge was calculated for each animal. The AUC value of each animal at each challenge was normalized to the mean AUC value of Group 1. Mean±SEM of normalized AUC was calculated for each group for each challenge and is shown in Table 17 and FIG. 2. Statistical analyses were performed by one-way ANOVA followed by Bonferroni post-hoc tests, comparing Groups 1, 3, 4, or 5 to Group 2, for each challenge.

Compared with animals administered with isotype control on Day 0 and saline on days of Exendin-4 challenge (Group 1), animals administered with isotype control on Day 0 and Exendin-4 on days of Exendin-4 challenge (Group 2) showed Exendin-4 induced reductions in normalized glucose AUC on each day the challenge was performed. Animals administered with Exendin-9 (Group 3) showed correction of Exendin-4 induced hypoglycemia when Exendin-4 challenge was performed 30 minutes post Exendin-9 administration, but not when the challenge was performed 4.5 or 24 hours post Exendin-9 administration. Animals administered with a single, 3 mg/kg dose of mAb36986 (Group 4) showed correction of Exendin-4 induced hypoglycemia when Exendin-4 challenge was performed 1, 3, 7, 15, 21, and 29 days post mAb36986 administration, but not when the challenge was performed 65 and 80 days post mAb36986 administration. Animals administered with a single, 10 mg/kg dose of mAb36986 (Group 5) showed correction of Exendin-4 induced hypoglycemia when Exendin-4 challenge was performed 1, 3, 7, 15, 21, 29, and 65 days post mAb36986 administration, but not when the challenge was performed 80 days post mAb36986 administration.

The data demonstrate that a single dose of mAb36986 can correct GLP1-induced hypoglycemia for one to two months in mice and that the duration action is dose-dependent, whereas a single dose of Exendin-9 corrects GLP-1 induced hypoglycemia for 4 hours or less. In conclusion, the GLP1R antagonist antibody of the disclosure, mAb36986, corrected GLP1-induced hypoglycemia with a long and dose-dependent duration action.

TABLE 17

Normalized glucose area under the curve (AUC) during exendin-4 challenges performed hours (h) or days (d) post test article administration

| Group | Test article administered on Day 0 | Compound administered at 0-min timepoint of Exendin-4 challenge | Time of Exendin-4 challenge post test article administration | Normalized glucose AUC during Exendin-4 challenge (% of Group 1) Mean | SEM |
|---|---|---|---|---|---|
| 1 | Isotype control | Saline | 1 d (= 24 h) | 100.0**** | 4.4 |
|   |   |   | 3 d | 100.0**** | 2.6 |
|   |   |   | 7 d | 100.0**** | 2.5 |
|   |   |   | 15 d | 100.0**** | 3.0 |
|   |   |   | 21 d | 100.0**** | 1.2 |
|   |   |   | 29 d | 100.0**** | 2.6 |
|   |   |   | 65 d | 100.0**** | 4.6 |
|   |   |   | 80 d | 100.0**** | 4.9 |
| 2 | Isotype control | Exendin-4 | 1 d (= 24 h) | 62.7 | 3.7 |
|   |   |   | 3 d | 69.5 | 4.3 |
|   |   |   | 7 d | 64.2 | 2.9 |
|   |   |   | 15 d | 65.1 | 2.9 |
|   |   |   | 21 d | 69.2 | 7.0 |
|   |   |   | 29 d | 62.8 | 3.2 |
|   |   |   | 65 d | 62.3 | 2.8 |
|   |   |   | 80 d | 62.9 | 5.9 |
| 3 | Exendin-9 | Exendin-4 | 0.5 h | 101.3**** | 4.4 |
|   |   |   | 4.5 h | 70.1 | 2.3 |
|   |   |   | 24 h | 74.1 | 5.8 |
| 4 | mAb36986 (3 mg/kg) | Exendin-4 | 1 d (= 24 h) | 96.5**** | 2.6 |
|   |   |   | 3 d | 108.7**** | 3.7 |
|   |   |   | 7 d | 108.6**** | 2.9 |
|   |   |   | 15 d | 102.2**** | 4.3 |
|   |   |   | 21 d | 93.2*** | 3.1 |
|   |   |   | 29 d | 84.0*** | 3.4 |
|   |   |   | 65 d | 67.4 | 2.6 |
|   |   |   | 80 d | 70.4 | 5.7 |
| 5 | mAb36986 (10 mg/kg) | Exendin-4 | 1 d (= 24 h) | 106.7**** | 5.4 |
|   |   |   | 3 d | 116.6**** | 5.3 |
|   |   |   | 7 d | 107.7**** | 1.6 |
|   |   |   | 15 d | 107.5**** | 2.9 |
|   |   |   | 21 d | 108.7**** | 2.9 |
|   |   |   | 29 d | 103.5**** | 4.5 |
|   |   |   | 65 d | 95.8**** | 3.8 |
|   |   |   | 80 d | 74.2 | 3.1 |

*$P < 0.001$, **$P < 0.0001$, compared to Group 2.

The present disclosure is not to be limited in scope by the specific embodiments described herein. Indeed, various modifications in addition to those described herein will become apparent to those skilled in the art from the foregoing description and the accompanying figures. Such modifications are intended to fall within the scope of the appended claims.

What is claimed is:

1. An isolated polynucleotide molecule comprising a polynucleotide sequence that encodes a heavy chain variable region (HCVR) and/or a light chain variable region (LCVR) of an antibody or antigen-binding fragment thereof that binds specifically to glucagon-like peptide 1 receptor (GLP1R) protein, wherein the antibody or antigen-binding fragment thereof attenuates GLP1R activity and elevates blood glucose levels, and wherein the antibody or antigen-binding fragment thereof comprises three heavy chain complementarity determining regions (CDRs) (HCDR1, HCDR2 and HCDR3) contained within the HCVR, and three light chain CDRs (LCDR1, LCDR2 and LCDR3) contained within the LCVR, wherein HCDR1 comprises the amino acid sequence of SEQ ID NO: 4, HCDR2 comprises the amino acid sequence of SEQ ID NO: 6, HCDR3 comprises the amino acid sequence of SEQ ID NO: 8, LCDR1 comprises the amino acid sequence of SEQ ID NO: 12, LCDR2 comprises the amino acid sequence of SEQ ID NO: 14, and LCDR3 comprises the amino acid sequence of SEQ ID NO: 16, wherein:

the HCVR comprises:
(i) an amino acid sequence of SEQ ID NO: 2;
(ii) an amino acid sequence having at least 90% identity to the amino acid sequence of SEQ ID NO: 2;
(iii) an amino acid sequence having at least 95% identity to the amino acid sequence of SEQ ID NO: 2; or
(iv) an amino acid sequence of SEQ ID NO: 2 having no more than 12 amino acid substitutions; and the LCVR comprises:
(i) an amino acid sequence of SEQ ID NO: 10;
(ii) an amino acid sequence having at least 90% identity to the amino acid sequence of SEQ ID NO: 10;
iii) an amino acid sequence having at least 95% identity to the amino acid sequence of SEQ ID NO: 10; or
(iv) an amino acid sequence of SEQ ID NO: 10 having no more than 12 amino acid substitutions.

2. An isolated vector comprising the polynucleotide molecule of claim 1.

3. An isolated host cell expressing the vector of claim 2.

4. The isolated host cell of claim 3 expressing a first vector comprising a polynucleotide sequence that encodes the HCVR and a second vector comprising a polynucleotide sequence that encodes the LCVR.

5. A method of producing an anti-GLP1R antagonist antibody or antigen-binding fragment thereof, comprising growing the host cell of claim 4 under conditions permitting production of the antibody or fragment, and recovering the antibody or fragment so produced.

6. An isolated polynucleotide molecule comprising a polynucleotide sequence that encodes a heavy chain variable region (HCVR) and/or a light chain variable region (LCVR) of an antibody or antigen-binding fragment thereof that binds specifically to glucagon-like peptide 1 receptor (GLP1R) protein, wherein the antibody or antigen-binding fragment thereof attenuates GLP1R activity and elevates blood glucose levels, and wherein the antibody or antigen-binding fragment thereof comprises three heavy chain complementarity determining regions (CDRs) (HCDR1, HCDR2 and HCDR3) contained within the HCVR, and three light chain CDRs (LCDR1, LCDR2 and LCDR3) contained within the LCVR, wherein HCDR1 comprises the amino acid sequence of SEQ ID NO: 24, HCDR2 comprises the amino acid sequence of SEQ ID NO: 26, HCDR3 comprises the amino acid sequence of SEQ ID NO: 28, LCDR1 comprises the amino acid sequence of SEQ ID NO: 32, LCDR2 comprises the amino acid sequence of SEQ ID NO: 14, and LCDR3 comprises the amino acid sequence of SEQ ID NO: 34, wherein:

the HCVR comprises:
(i) an amino acid sequence of SEQ ID NO: 22;
(ii) an amino acid sequence having at least 90% identity to the amino acid sequence of SEQ ID NO: 22;
(iii) an amino acid sequence having at least 95% identity to the amino acid sequence of SEQ ID NO: 22; or
(iv) an amino acid sequence of SEQ ID NO: 22 having no more than 12 amino acid substitutions; and the LCVR comprises:
(i) an amino acid sequence of SEQ ID NO: 30;
(ii) an amino acid sequence having at least 90% identity to the amino acid sequence of SEQ ID NO: 30;
(iii) an amino acid sequence having at least 95% identity to the amino acid sequence of SEQ ID NO: 30; or
(iv) an amino acid sequence of SEQ ID NO: 30 having no more than 12 amino acid substitutions.

7. An isolated vector comprising the polynucleotide molecule of claim 6.

8. An isolated host cell expressing the vector of claim 7.

9. The isolated host cell of claim 8 expressing a first vector comprising a polynucleotide sequence that encodes the HCVR and a second vector comprising a polynucleotide sequence that encodes the LCVR.

10. A method of producing an anti-GLP1R antagonist antibody or antigen-binding fragment thereof, comprising growing the host cell of claim 9 under conditions permitting production of the antibody or fragment, and recovering the antibody or fragment so produced.

11. An isolated polynucleotide molecule comprising a polynucleotide sequence that encodes a heavy chain variable region (HCVR) and/or a light chain variable region (LCVR) of an antibody or antigen-binding fragment thereof that binds specifically to glucagon-like peptide 1 receptor (GLP1R) protein, wherein the antibody or antigen-binding fragment thereof attenuates GLP1R activity and elevates blood glucose levels, and wherein the antibody or antigen-binding fragment thereof comprises three heavy chain complementarity determining regions (CDRs) (HCDR1, HCDR2 and HCDR3) contained within the HCVR, and three light chain CDRs (LCDR1, LCDR2 and LCDR3) contained within the LCVR, wherein HCDR1 comprises the amino acid sequence of SEQ ID NO: 42, HCDR2 comprises the amino acid sequence of SEQ ID NO: 44, HCDR3 comprises the amino acid sequence of SEQ ID NO: 46, LCDR1 comprises the amino acid sequence of SEQ ID NO: 50, LCDR2 comprises the amino acid sequence of SEQ ID NO: 52, and LCDR3 comprises the amino acid sequence of SEQ ID NO: 54, wherein:

the HCVR comprises:
(i) an amino acid sequence of SEQ ID NO: 40;
(ii) an amino acid sequence having at least 90% identity to the amino acid sequence of SEQ ID NO: 40;
(iii) an amino acid sequence having at least 95% identity to the amino acid sequence of SEQ ID NO: 40; or
(iv) an amino acid sequence of SEQ ID NO: 40 having no more than 12 amino acid substitutions; and the LCVR comprises:
(i) an amino acid sequence of SEQ ID NO: 48;
(ii) an amino acid sequence having at least 90% identity to the amino acid sequence of SEQ ID NO: 48;
(iii) an amino acid sequence having at least 95% identity to the amino acid sequence of SEQ ID NO: 48; or
(iv) an amino acid sequence of SEQ ID NO: 48 having no more than 12 amino acid substitutions.

12. An isolated vector comprising the polynucleotide molecule of claim 11.

13. An isolated host cell expressing the vector of claim 12.

14. The isolated host cell of claim 13 expressing a first vector comprising a polynucleotide sequence that encodes the HCVR and a second vector comprising a polynucleotide sequence that encodes the LCVR.

15. A method of producing an anti-GLP1R antagonist antibody or antigen-binding fragment thereof, comprising growing the host cell of claim 14 under conditions permitting production of the antibody or fragment, and recovering the antibody or fragment so produced.

\* \* \* \* \*

SEQUENCE LISTING

```
Sequence total quantity: 63
SEQ ID NO: 1            moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 1
caggttcagc tggtgcagtc tggaactgag gttaagaagc ctggggcctc agtgaaggtc  60
tcctgcatgg cttctggtta cacctttacc acctatggta tcagctgggt gcgacaggcc 120
cctggacaag ggcttgagtg gatggggtgg atcagcgctt acaatggtaa cacaaagtat 180
gcacagaggc tccagggcag agtcaccatg accacagaca catccacgac cacagcctac 240
atggggctga ggggcctgag atctgacgac acggccgtgt atttctgtgc gagagtcacc 300
ttgtcaggaa gatttgacta ctggggccag ggaaccctgg tcaccgtctc tcca         354

SEQ ID NO: 2            moltype = AA  length = 118
FEATURE                 Location/Qualifiers
REGION                  1..118
                        note = Synthetic
source                  1..118
                        mol_type = protein
                        organism = synthetic construct
SEQUENCE: 2
QVQLVQSGTE VKKPGASVKV SCMASGYTFT TYGISWVRQA PGQGLEWMGW ISAYNGNTKY  60
AQRLQGRVTM TTDTSTTTAY MGLRGLRSDD TAVYFCARVT LSGRFDYWGQ GTLVTVSP   118

SEQ ID NO: 3            moltype = DNA  length = 24
FEATURE                 Location/Qualifiers
misc_feature            1..24
                        note = Synthetic
source                  1..24
                        mol_type = other DNA
```

```
                                 -continued
                organism = synthetic construct
SEQUENCE: 3
ggttacacct ttaccaccta tggt                                           24

SEQ ID NO: 4          moltype = AA   length = 8
FEATURE               Location/Qualifiers
REGION                1..8
                      note = Synthetic
source                1..8
                      mol_type = protein
                      organism = synthetic construct
SEQUENCE: 4
GYTFTTYG                                                              8

SEQ ID NO: 5          moltype = DNA  length = 24
FEATURE               Location/Qualifiers
misc_feature          1..24
                      note = Synthetic
source                1..24
                      mol_type = other DNA
                      organism = synthetic construct
SEQUENCE: 5
atcagcgctt acaatggtaa caca                                           24

SEQ ID NO: 6          moltype = AA   length = 8
FEATURE               Location/Qualifiers
REGION                1..8
                      note = Synthetic
source                1..8
                      mol_type = protein
                      organism = synthetic construct
SEQUENCE: 6
ISAYNGNT                                                              8

SEQ ID NO: 7          moltype = DNA  length = 33
FEATURE               Location/Qualifiers
misc_feature          1..33
                      note = Synthetic
source                1..33
                      mol_type = other DNA
                      organism = synthetic construct
SEQUENCE: 7
gcgagagtca ccttgtcagg aagatttgac tac                                 33

SEQ ID NO: 8          moltype = AA   length = 11
FEATURE               Location/Qualifiers
REGION                1..11
                      note = Synthetic
source                1..11
                      mol_type = protein
                      organism = synthetic construct
SEQUENCE: 8
ARVTLSGRFD Y                                                         11

SEQ ID NO: 9          moltype = DNA  length = 321
FEATURE               Location/Qualifiers
misc_feature          1..321
                      note = Synthetic
source                1..321
                      mol_type = other DNA
                      organism = synthetic construct
SEQUENCE: 9
gacatccaga tgacccagtc tccatcctcc ctgtctgcat ctgtaggaga cagagtcacc     60
atcacttgcc aggcgagtca ggacattagc gactatttaa attggtatca gcagaaacca   120
gggaaagccc ctaaactcct gatctacgat gcatccaatt tggaaacagg ggtcccatca   180
cgattcagtg aagtggatc tgggacagat tttactttca ccatccgcag cctgcagcct   240
gaagatattg caacatatta ctgtcaacaa tatgataatc tcccgtacac ttttggccag   300
gggaccaagc tggagatcaa a                                            321

SEQ ID NO: 10         moltype = AA   length = 107
FEATURE               Location/Qualifiers
REGION                1..107
                      note = Synthetic
source                1..107
                      mol_type = protein
                      organism = synthetic construct
SEQUENCE: 10
DIQMTQSPSS LSASVGDRVT ITCQASQDIS DYLNWYQQKP GKAPKLLIYD ASNLETGVPS     60
RFSGSGSGTD FTFTIRSLQP EDIATYYCQQ YDNLPYTFGQ GTKLEIK                 107
```

```
SEQ ID NO: 11              moltype = DNA   length = 18
FEATURE                    Location/Qualifiers
misc_feature               1..18
                           note = Synthetic
source                     1..18
                           mol_type = other DNA
                           organism = synthetic construct
SEQUENCE: 11
caggacatta gcgactat                                                  18

SEQ ID NO: 12              moltype = AA   length = 6
FEATURE                    Location/Qualifiers
REGION                     1..6
                           note = Synthetic
source                     1..6
                           mol_type = protein
                           organism = synthetic construct
SEQUENCE: 12
QDISDY                                                                6

SEQ ID NO: 13              moltype =   length =
SEQUENCE: 13
000

SEQ ID NO: 14              moltype =   length =
SEQUENCE: 14
000

SEQ ID NO: 15              moltype = DNA   length = 27
FEATURE                    Location/Qualifiers
misc_feature               1..27
                           note = Synthetic
source                     1..27
                           mol_type = other DNA
                           organism = synthetic construct
SEQUENCE: 15
caacaatatg ataatctccc gtacact                                        27

SEQ ID NO: 16              moltype = AA   length = 9
FEATURE                    Location/Qualifiers
REGION                     1..9
                           note = Synthetic
source                     1..9
                           mol_type = protein
                           organism = synthetic construct
SEQUENCE: 16
QQYDNLPYT                                                             9

SEQ ID NO: 17              moltype = DNA   length = 1338
FEATURE                    Location/Qualifiers
misc_feature               1..1338
                           note = Synthetic
source                     1..1338
                           mol_type = other DNA
                           organism = synthetic construct
SEQUENCE: 17
caggttcagc tggtgcagtc tggaactgag gttaagaagc ctggggcctc agtgaaggtc    60
tcctgcatgg cttctggtta caccttttacc acctatggta tcagctgggt gcgacaggcc   120
cctggacaag ggcttgagtg gatggggtgg atcagcgctt acaatggtaa cacaaagtat   180
gcacagaggc tccagggcag agtcaccatg accacagaca catccacgac acagcctac    240
atggggctga gggggcctgag atctgacgac acggccgtgt atttctgtgc gagagtcacc   300
ttgtcaggaa gatttgacta ctggggccag ggaaccctgg tcaccgtctc tccagcctcc   360
accaagggcc catcggtctt ccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct gggcacgaa gacctacacc    600
tgcaacgtag atcacaagcc cagcaacacc aaggtggaca gagagttga gtccaaatat    660
ggtcccccat gcccaccctg cccagcacct gagttcctgg ggggaccatc agtcttcctg   720
ttcccccaa acccaaggga cactctcatg atctcccgga cccctgaggt cacgtgcgtg   780
gtggtggacg tgagccagga agaccccgag gtccagttca actggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtctccaaca aaggcctccc gtcctccatc gagaaaacca tctccaaagc caaagggcaga  1020
ccccgagagc cacaggtgta caccctgccc ccatcccagg aggagatgac caagaaccag   1080
gtcagcctga cctgcctggt caaaggcttc taccccagcg acatcgccgt ggagtgggag   1140
agcaatgggc agccggagaa caactacaag accacgcctc ccgtgctgga ctccgacggc   1200
tccttcttcc tctacagcag gctcaccgtg gacaagagca ggtggcagga ggggaatgtc   1260
ttctcatgct ccgtgatgca tgaggctctg cacaaccact acacacagaa gtccctctcc   1320
```

```
ctgtctctgg gtaaatga                                                  1338

SEQ ID NO: 18            moltype = AA  length = 445
FEATURE                  Location/Qualifiers
REGION                   1..445
                         note = Synthetic
source                   1..445
                         mol_type = protein
                         organism = synthetic construct
SEQUENCE: 18
QVQLVQSGTE VKKPGASVKV SCMASGYTFT TYGISWVRQA PGQGLEWMGW ISAYNGNTKY    60
AQRLQGRVTM TTDTSTTTAY MGLRGLRSDD TAVYFCARVT LSGRFDYWGQ GTLVTVSPAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGK                                         445

SEQ ID NO: 19            moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 19
gacatccaga tgacccagtc tccatcctcc ctgtctgcat ctgtaggaga cagagtcacc    60
atcacttgcc aggcgagtca ggacattagc gactatttaa attggtatca gcagaaacca    120
gggaaagccc ctaaactcct gatctacgat gcatccaatt tggaaacagg ggtcccatca    180
cgattcagtg gaagtggatc tgggacagat tttactttca ccatccgcag cctgcagcct    240
gaagatattg caacatatta ctgtcaacaa tatgataatc tccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645

SEQ ID NO: 20            moltype = AA  length = 214
FEATURE                  Location/Qualifiers
REGION                   1..214
                         note = Synthetic
source                   1..214
                         mol_type = protein
                         organism = synthetic construct
SEQUENCE: 20
DIQMTQSPSS LSASVGDRVT ITCQASQDIS DYLNWYQQKP GKAPKLLIYD ASNLETGVPS    60
RFSGSGSGTD FTFTIRSLQP EDIATYYCQQ YDNLPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 21            moltype = DNA  length = 375
FEATURE                  Location/Qualifiers
misc_feature             1..375
                         note = Synthetic
source                   1..375
                         mol_type = other DNA
                         organism = synthetic construct
SEQUENCE: 21
gaggtgcagc tgttggagtc tgggggaggc gtggtacagc ctgggggtc cctgagactc     60
tcctgtgtag cctctggatt cacctttagc agctatgcca tgagctgggt ccgccaggct    120
ccagggaagg ggctggagtg ggtctcaagt atcagtggaa gtggtggtag tacagacaac    180
gcagactccg tgaagggccg gttcaccatc tccagagaca acgccaagaa cacgctgtat    240
ctgcaaatga acagcctgag agccgaggac acggccgtat attactgtgc aaaagatcga    300
attacgattt ttggagtggt tcttaacggt gcttttgata tctgggccca agggacaatg    360
gtcaccgtct cttca                                                    375

SEQ ID NO: 22            moltype = AA  length = 125
FEATURE                  Location/Qualifiers
REGION                   1..125
                         note = Synthetic
source                   1..125
                         mol_type = protein
                         organism = synthetic construct
SEQUENCE: 22
EVQLLESGGG VVQPGGSLRL SCVASGFTFS SYAMSWVRQA PGKGLEWVSS ISGSGGSTDN    60
ADSVKGRFTI SRDNSKNTLY LQMNSLRAED TAVYYCAKDR ITIFGVVLNG AFDIWGQGTM    120
VTVSS                                                               125
```

```
SEQ ID NO: 23              moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 23
ggattcacct ttagcagcta tgcc                                          24

SEQ ID NO: 24              moltype = AA  length = 8
FEATURE                    Location/Qualifiers
REGION                     1..8
                           note = Synthetic
source                     1..8
                           mol_type = protein
                           organism = synthetic construct
SEQUENCE: 24
GFTFSSYA                                                             8

SEQ ID NO: 25              moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 25
atcagtggaa gtggtggtag taca                                          24

SEQ ID NO: 26              moltype = AA  length = 8
FEATURE                    Location/Qualifiers
REGION                     1..8
                           note = Synthetic
source                     1..8
                           mol_type = protein
                           organism = synthetic construct
SEQUENCE: 26
ISGSGGST                                                             8

SEQ ID NO: 27              moltype = DNA  length = 54
FEATURE                    Location/Qualifiers
misc_feature               1..54
                           note = Synthetic
source                     1..54
                           mol_type = other DNA
                           organism = synthetic construct
SEQUENCE: 27
gcgaaagatc gaattacgat ttttggagtg gttcttaacg gtgcttttga tatc         54

SEQ ID NO: 28              moltype = AA  length = 18
FEATURE                    Location/Qualifiers
REGION                     1..18
                           note = Synthetic
source                     1..18
                           mol_type = protein
                           organism = synthetic construct
SEQUENCE: 28
AKDRITIFGV VLNGAFDI                                                 18

SEQ ID NO: 29              moltype = DNA  length = 318
FEATURE                    Location/Qualifiers
misc_feature               1..318
                           note = Synthetic
source                     1..318
                           mol_type = other DNA
                           organism = synthetic construct
SEQUENCE: 29
gacatccaga tgacccagtc tccatcctcc ctgtctgcat ctgtaggaga cagagtcacc    60
atcacttgcc aggcgagtca ggacattagg aactatttaa attggtatca acagaaacca   120
gggaaagccc ctaagctcct gatctacgat gcatccaatt tggaaacagg ggtcccatca   180
aggttcagtg aagtggatc tgggacagat tttactttca ccatcagcag cctgcagcct   240
gaagatattg caacatattt ctgtcaacag tatgataatc tattcacttt cggccctggg   300
accaaagtgg atatcaaa                                                318

SEQ ID NO: 30              moltype = AA  length = 106
FEATURE                    Location/Qualifiers
REGION                     1..106
```

```
                        note = Synthetic
source                  1..106
                        mol_type = protein
                        organism = synthetic construct
SEQUENCE: 30
DIQMTQSPSS LSASVGDRVT ITCQASQDIR NYLNWYQQKP GKAPKLLIYD ASNLETGVPS    60
RFSGSGSGTD FTFTISSLQP EDIATYFCQQ YDNLFTFGPG TKVDIK                  106

SEQ ID NO: 31           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 31
caggacatta ggaactat                                                  18

SEQ ID NO: 32           moltype = AA  length = 6
FEATURE                 Location/Qualifiers
REGION                  1..6
                        note = Synthetic
source                  1..6
                        mol_type = protein
                        organism = synthetic construct
SEQUENCE: 32
QDIRNY                                                                6

SEQ ID NO: 33           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 33
caacagtatg ataatctatt cact                                           24

SEQ ID NO: 34           moltype = AA  length = 8
FEATURE                 Location/Qualifiers
REGION                  1..8
                        note = Synthetic
source                  1..8
                        mol_type = protein
                        organism = synthetic construct
SEQUENCE: 34
QQYDNLFT                                                              8

SEQ ID NO: 35           moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 35
gaggtgcagc tgttggagtc tgggggaggc gtggtacagc ctgggggggtc cctgagactc    60
tcctgtgtag cctctggatt cacctttagc agctatgcca tgagctgggt ccgccaggct   120
ccagggaagg ggctggagtg ggtctcaagt atcagtggaa gtggtggtag tacagacaac   180
gcagactccg tgaagggccg gttcaccatc tccagagaca attccaagaa cacgctgtat   240
ctgcaaatga acagcctgag agccgaggac acggccgtat attactgtgc gaaagatcga   300
attacgattt ttggagtggt tcttaacggt gcttttgata tctggggcca agggacaatg   360
gtcaccgtct cttcagcctc caccaagggc ccatcggtct tccccctggc gccctgctcc   420
aggagcacct ccgagagcac agccgccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcacga gacctacac ctgcaacgta gatcacaagc ccagcaacac caaggtggac   660
aagagagttg agtccaaata tggtcccccca tgcccaccct gcccagcagc tgagttcctg   720
gggggaccat cagtcttcct gttccccccca aaacccaagg acactctcat gatctcccgg   780
acccctgagg tcacgtgcgt ggtggtggac gtgagccagg aagaccccga ggtccagttc   840
aactggtacg tggatggcgt ggaggtgcat aatgccaaga caaagccgcg ggaggagcag   900
ttcaacagca cgtaccgtgt ggtcagcgtc ctcaccgtcc tgcaccagga ctggctgaac   960
ggcaaggagt acaagtgcaa ggtctccaac aaaggcctcc cgtcctccat cgagaaaacc  1020
atctccaaag ccaaagggca gccccgagag ccacaggtgt acaccctgcc cccatcccag  1080
gaggagatga ccaagaacca ggtcagcctg acctgcctgg tcaaaggctt ctaccccagc  1140
gacatcgccg tggagtggga gagcaatggg cagccggaga caactacaa gaccacgcct  1200
cccgtgctga ctccgacgg ctccttcttc ctctacagca ggctcaccgt ggacaagagc  1260
aggtggcagg aggggaatgt cttctcatgc tccgtgatgc atgaggctct gcacaaccac  1320
tacacacaga agtccctctc cctgtctctg ggtaaatga                        1359
```

```
SEQ ID NO: 36           moltype = AA  length = 452
FEATURE                 Location/Qualifiers
REGION                  1..452
                        note = Synthetic
source                  1..452
                        mol_type = protein
                        organism = synthetic construct
SEQUENCE: 36
EVQLLESGGG VVQPGGSLRL SCVASGFTFS SYAMSWVRQA PGKGLEWVSS ISGSGGSTDN   60
ADSVKGRFTI SRDNSKNTLY LQMNSLRAED TAVYYCAKDR ITIFGVVLNG AFDIWGQGTM  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GK                                452

SEQ ID NO: 37           moltype = DNA  length = 642
FEATURE                 Location/Qualifiers
misc_feature            1..642
                        note = Synthetic
source                  1..642
                        mol_type = other DNA
                        organism = synthetic construct
SEQUENCE: 37
gacatccaga tgacccagtc tccatcctcc ctgtctgcat ctgtaggaga cagagtcacc   60
atcacttgcc aggcgagtca ggacattagg aactatttaa attggtatca acagaaacca  120
gggaaagccc ctaagctcct gatctacgat gcatccaatt tggaaacagg gtcccatca   180
aggttcagtg gaagtggatc tgggacagat tttactttca ccatcagcag cctgcagcct  240
gaagatattg caacatattt ctgtcaacag tatgataatc tattcacttt cggccctggg  300
accaaagtgg atatcaaacg aactgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcaggcctg   600
agctcgcccg tcacaaagag cttcaacagg ggagagtgtt ag                     642

SEQ ID NO: 38           moltype = AA  length = 213
FEATURE                 Location/Qualifiers
REGION                  1..213
                        note = Synthetic
source                  1..213
                        mol_type = protein
                        organism = synthetic construct
SEQUENCE: 38
DIQMTQSPSS LSASVGDRVT ITCQASQDIR NYLNWYQQKP GKAPKLLIYD ASNLETGVPS   60
RFSGSGSGTD FTFTISSLQP EDIATYFCQQ YDNLFTFGPG TKVDIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 39           moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 39
caagtgcgcc tacagcagtg gggcgcagga ctgttgaagc cttcggagac cctgtccctc   60
acctgcgctg tctatggtgg gtccttcagt ggttacttct ggagctggat ccgccagccc  120
ccagggaagg gactggagtg gattggggaa atcaatcatg gtggaaacac caactccaac  180
ccgtccctca gagtcgagt caccatatca gtggacacgt ccaagaacca gttctccctg   240
aaactgagtg ctgtgatcgc cgcggacacg gctgtatatt actgtgcgag aggccagtat  300
cgcagtggcg gagggtactg gtacttcgat ctctggggcc gtggcaccct ggtcacagtc  360
tcctca                                                              366

SEQ ID NO: 40           moltype = AA  length = 122
FEATURE                 Location/Qualifiers
REGION                  1..122
                        note = Synthetic
source                  1..122
                        mol_type = protein
                        organism = synthetic construct
SEQUENCE: 40
QVRLQQWGAG LLKPSETLSL TCAVYGGSFS GYFWSWIRQP PGKGLEWIGE INHGGNTNSN   60
PSLKSRVTIS VDTSKNQFSL KLSAVIAADT AVYYCARGQY RSGGGYWYFD LWGRGTLVTV  120
SS                                                                  122
```

```
SEQ ID NO: 41              moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 41
ggtgggtcct tcagtggtta cttc                                           24

SEQ ID NO: 42              moltype = AA  length = 8
FEATURE                    Location/Qualifiers
REGION                     1..8
                           note = Synthetic
source                     1..8
                           mol_type = protein
                           organism = synthetic construct
SEQUENCE: 42
GGSFSGYF                                                              8

SEQ ID NO: 43              moltype = DNA  length = 21
FEATURE                    Location/Qualifiers
misc_feature               1..21
                           note = Synthetic
source                     1..21
                           mol_type = other DNA
                           organism = synthetic construct
SEQUENCE: 43
atcaatcatg gtggaaacac c                                              21

SEQ ID NO: 44              moltype = AA  length = 7
FEATURE                    Location/Qualifiers
REGION                     1..7
                           note = Synthetic
source                     1..7
                           mol_type = protein
                           organism = synthetic construct
SEQUENCE: 44
INHGGNT                                                               7

SEQ ID NO: 45              moltype = DNA  length = 48
FEATURE                    Location/Qualifiers
misc_feature               1..48
                           note = Synthetic
source                     1..48
                           mol_type = other DNA
                           organism = synthetic construct
SEQUENCE: 45
gcgagaggcc agtatcgcag tggcggaggg tactggtact tcgatctc                 48

SEQ ID NO: 46              moltype = AA  length = 16
FEATURE                    Location/Qualifiers
REGION                     1..16
                           note = Synthetic
source                     1..16
                           mol_type = protein
                           organism = synthetic construct
SEQUENCE: 46
ARGQYRSGGG YWYFDL                                                    16

SEQ ID NO: 47              moltype = DNA  length = 324
FEATURE                    Location/Qualifiers
misc_feature               1..324
                           note = Synthetic
source                     1..324
                           mol_type = other DNA
                           organism = synthetic construct
SEQUENCE: 47
gaaattgtgt tgacgcagtc tccaggcacc ctctctttgt ctccagggga aagagccacc    60
ctctcctgca gggccagtca gagtattagc agtgtccact tagcctggta tcagcagaaa   120
cctggccagg ctcccaggct cctcatctat ggtgcatcca gcagggccac tggcatccca   180
gacaggttca gtgcagtggg gtctgagaca gacttcactc tcaccgtcag cagactggag   240
cctgatgatt ttacaatgta ttactgtcag caatatggta gctcaccttg gacgttcggc   300
caagggacca aggtggaaat caaa                                          324

SEQ ID NO: 48              moltype = AA  length = 108
FEATURE                    Location/Qualifiers
REGION                     1..108
                           note = Synthetic
```

```
source                   1..108
                         mol_type = protein
                         organism = synthetic construct
SEQUENCE: 48
EIVLTQSPGT LSLSPGERAT LSCRASQSIS SVHLAWYQQK PGQAPRLLIY GASSRATGIP    60
DRFSGSGSET DFTLTVSRLE PDDFTMYYCQ QYGSSPWTFG QGTKVEIK                108

SEQ ID NO: 49            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 49
cagagtatta gcagtgtcca c                                              21

SEQ ID NO: 50            moltype = AA  length = 7
FEATURE                  Location/Qualifiers
REGION                   1..7
                         note = Synthetic
source                   1..7
                         mol_type = protein
                         organism = synthetic construct
SEQUENCE: 50
QSISSVH                                                              7

SEQ ID NO: 51            moltype =  length =
SEQUENCE: 51
000

SEQ ID NO: 52            moltype =  length =
SEQUENCE: 52
000

SEQ ID NO: 53            moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 53
cagcaatatg gtagctcacc ttggacg                                        27

SEQ ID NO: 54            moltype = AA  length = 9
FEATURE                  Location/Qualifiers
REGION                   1..9
                         note = Synthetic
source                   1..9
                         mol_type = protein
                         organism = synthetic construct
SEQUENCE: 54
QQYGSSPWT                                                            9

SEQ ID NO: 55            moltype = DNA  length = 1350
FEATURE                  Location/Qualifiers
misc_feature             1..1350
                         note = Synthetic
source                   1..1350
                         mol_type = other DNA
                         organism = synthetic construct
SEQUENCE: 55
caagtgcgcc tacagcagtg gggcgcagga ctgttgaagc cttcggagac cctgtccctc    60
acctgcgctg tctatggtgg gtccttcagt ggttacttct ggagctggat ccgccagccc   120
ccagggaagg gactggagtg gattggggaa atcaatcatg gtggaaacac caactccaac   180
ccgtccctca gagtcgagt caccatatca gtggacacgt ccaagaacca gttctccctg    240
aaactgagtg ctgtgatcgc cgcggacacg gctgtatatt actgtgcgag aggccagtat   300
cgcagtggcg gagggtactg gtacttcgat tctctgggcc gtggcaccct ggtcacagtc   360
tcctcagcct ccaccaaggg cccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccaccc tgcccagcac ctgagttcct ggggggacca   720
tcagtcttcc tgttcccccc aaaacccaag gacactctca tgatccccg acccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag   960
```

```
tacaagtgca aggtctccaa caaaggcctc ccgtcctcca tcgagaaaac catctccaaa   1020
gccaaagggc agccccgaga gccacaggta tacaccctgc ccccatccca ggaggagatg   1080
accaagaacc aggtcagcct gacctgcctg gtcaaaggct tctacccag cgacatcgcc   1140
gtggagtggg agagcaatgg gcagccggag aacaactaca agaccacgcc tcccgtgctg   1200
gactccgacg gctccttctt cctctacagc aggctcaccg tggacaagag caggtggcag   1260
gagggaatg tcttctcatg ctccgtgatg catgaggctc tgcacaacca ctacacacag   1320
aagtccctct ccctgtctct gggtaaatga                                     1350

SEQ ID NO: 56          moltype = AA  length = 449
FEATURE                Location/Qualifiers
REGION                 1..449
                       note = Synthetic
source                 1..449
                       mol_type = protein
                       organism = synthetic construct
SEQUENCE: 56
QVRLQQWGAG LLKPSETLSL TCAVYGGSFS GYFWSWIRQP PGKGLEWIGE INHGGNTNSN    60
PSLKSRVTIS VDTSKNQFSL KLSAVIAADT AVYYCARGQY RSGGGYWYFD LWGRGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLGK                                     449

SEQ ID NO: 57          moltype = DNA  length = 648
FEATURE                Location/Qualifiers
misc_feature           1..648
                       note = Synthetic
source                 1..648
                       mol_type = other DNA
                       organism = synthetic construct
SEQUENCE: 57
gaaattgtgt tgacgcagtc tccaggcacc ctctctttgt ctccagggga aagagccacc    60
ctctcctgca gggccagtca gagtattagc agtgtccact tagcctggta tcagcagaaa   120
cctggccagg ctcccaggct cctcatctat ggtgcatcca gcagggccac tggcatccca   180
gacaggttca gtggcagtgg gtctgagaca gacttcactc tcaccgtcag cagactggag   240
cctgatgatt ttacaatgta ttactgtcag caatatggta gctcaccttg gacgttcggc   300
caagggacca aggtggaaat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttag                648

SEQ ID NO: 58          moltype = AA  length = 215
FEATURE                Location/Qualifiers
REGION                 1..215
                       note = Synthetic
source                 1..215
                       mol_type = protein
                       organism = synthetic construct
SEQUENCE: 58
EIVLTQSPGT LSLSPGERAT LSCRASQSIS SVHLAWYQQK PGQAPRLLIY GASSRATGIP    60
DRFSGSGSET DFTLTVSRLE PDDFTMYYCQ QYGSSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 59          moltype = AA  length = 144
FEATURE                Location/Qualifiers
REGION                 1..144
                       note = Human GLP1R-MMH
source                 1..144
                       mol_type = protein
                       organism = synthetic construct
SEQUENCE: 59
RPQGATVSLW ETVQKWREYR RQCQRSLTED PPPATDLFCN RTFDEYACWP DGEPGSFVNV    60
SCPWYLPWAS SVPQGHVYRF CTAEGLWLQK DNSSLPWRDL SECEESKRGE RSSPEEEQKL   120
ISEEDLGGEQ KLISEEDLHH HHHH                                          144

SEQ ID NO: 60          moltype = AA  length = 144
FEATURE                Location/Qualifiers
REGION                 1..144
                       note = Monkey GLP1R-MMH
source                 1..144
                       mol_type = protein
                       organism = synthetic construct
SEQUENCE: 60
RPQGATVSLW ETVQKWREYR RQCQRSLTED PPPATDLFCN RTFDEYACWP DGEPGSFVNV    60
```

```
SCPWYLPWAS SVPQGHVYRF CTAEGLWLQK DNSSLPWRDL SECEESKRGE RNSPEEEQKL    120
ISEEDLGGEQ KLISEEDLHH HHHH                                          144

SEQ ID NO: 61          moltype = AA  length = 152
FEATURE                Location/Qualifiers
REGION                 1..152
                       note = Mouse GLP1R-MMH
source                 1..152
                       mol_type = protein
                       organism = synthetic construct
SEQUENCE: 61
GPRPQGTTVS LSETVQKWRE YRRQCQRFLT EAPLLATGLF CNRTFDDYAC WPDGPPGSFV    60
NVSCPWYLPW ASSVLQGHVY RFCTAEGLWL HKDNSSLPWR DLSECEESKR GERNFPEEQL    120
LSLYEQKLIS EEDLGGEQKL ISEEDLHHHH HH                                 152

SEQ ID NO: 62          moltype = AA  length = 189
FEATURE                Location/Qualifiers
REGION                 1..189
                       note = hdesA-GLP1_GLP1R-MMH
source                 1..189
                       mol_type = protein
                       organism = synthetic construct
SEQUENCE: 62
HEGTFTSDVS SYLEGQAAKE FIAWLVKGRG GGGGSGGGGS GGGGSRPQGA TVSLWETVQK    60
WREYRRQCQR SLTEDPPPAT DLFCNRTFDE YACWPDGEPG SFVNVSCPWY LPWASSVPQG    120
HVYRFCTAEG LWLQKDNSSL PWRDLSECEE SKRGERSSPE EEQKLISEED LGGEQKLISE    180
EDLHHHHHH                                                           189

SEQ ID NO: 63          moltype = AA  length = 349
FEATURE                Location/Qualifiers
source                 1..349
                       mol_type = protein
                       organism = Homo sapiens
SEQUENCE: 63
RPQGATVSLW ETVQKWREYR RQCQRSLTED PPPATDLFCN RTFDEYACWP DGEPGSFVNV    60
SCPWYLPWAS SVPQGHVYRF CTAEGLWLQK DNSSLPWRDL SECEESKRGE RSSPEEEPRG    120
PTIKPCPPCK CPAPNLLGGP SVFIFPPKIK DVLMISLSPI VTCVVVDVSE DDPDVQISWF    180
VNNVEVHTAQ TQTHREDYNS TLRVVSALPI QHQDWMSGKE FKCKVNNKDL PAPIERTISK    240
PKGSVRAPQV YVLPPPEEEM TKKQVTLTCM VTDFMPEDIY VEWTNNGKTE LNYKNTEPVL    300
DSDGSYFMYS KLRVEKKNWV ERNSYSCSVV HEGLHNHHTT KSFSRTPGK               349
```